United States Patent
Wu et al.

(10) Patent No.: US 10,161,876 B2
(45) Date of Patent: *Dec. 25, 2018

(54) POLYDIACETYLENE AND POLYDIACETYLENE/ZNO NANOCOMPOSITE SENSORS

(71) Applicant: NEW JERSEY INSTITUTE OF TECHNOLOGY, Newark, NJ (US)

(72) Inventors: Aide Wu, Kearny, NJ (US); Zafar Iqbal, Morris Plains, NJ (US); John Federici, Westfield, NJ (US)

(73) Assignee: New Jersey Institute of Technology, Newark, NJ (US)

(*) Notice: Subject to any disclaimer, the term of this patent is extended or adjusted under 35 U.S.C. 154(b) by 504 days.

This patent is subject to a terminal disclaimer.

(21) Appl. No.: 14/842,965

(22) Filed: Sep. 2, 2015

(65) Prior Publication Data

US 2016/0061741 A1 Mar. 3, 2016

Related U.S. Application Data

(60) Provisional application No. 62/045,322, filed on Sep. 3, 2014, provisional application No. 62/044,790, filed on Sep. 2, 2014, provisional application No. 62/044,796, filed on Sep. 2, 2014.

(51) Int. Cl.
*G01N 21/78* (2006.01)
*C09K 9/02* (2006.01)
*G01N 21/75* (2006.01)

(52) U.S. Cl.
CPC ............... *G01N 21/78* (2013.01); *C09K 9/02* (2013.01); *C09K 2211/14* (2013.01); *G01N 2021/757* (2013.01)

(58) Field of Classification Search
CPC .................................. G01N 21/78; C09K 9/02
USPC ........................................................ 422/425
See application file for complete search history.

(56) References Cited

U.S. PATENT DOCUMENTS 8,722,418 B1 * 5/2014 Zunino, III .......... G01N 31/229
  252/408.1
2015/0329656 A1 * 11/2015 Kim ...................... C08F 138/00
  524/547

OTHER PUBLICATIONS

Chanakul, A. (2013). "Controlling the reversible thermochromism of polydiacetylene/zinc oxide nanocomposites by varying alkyl chain length." J Colloid and Interface Sci. 389(1):106-114. (Year: 2013).*

Patlolla, A. (2012). "Thermochromism in poly-diacetylene-metal oxide nanocomposites." J. Mater. Chem. 22:7028-7035. (Year: 2012).*

(Continued)

*Primary Examiner* — Jill A Warden
*Assistant Examiner* — Jacqueline Brazin
(74) *Attorney, Agent, or Firm* — Timothy X. Gibson, Esq.; Gibson & Dernier LLP

(57) ABSTRACT

Polydiacetylenes (PDAs) and PDA/ZnO nanocomposites based on the monomers: 10,12-pentacosadiynoic acid (PCDA), 10,12-tricosadiynoic acid (TCDA) and 10,12-docosadiynedioic acid (DCDA) monomers are chromatic chemical sensing agents for selected organic liquids. Thermochromically reversible compositions include PCDA and nanosize ZnO having a particle size range less than 100 nm.

12 Claims, 27 Drawing Sheets

(56) References Cited

OTHER PUBLICATIONS

Chanakul, A. et al. (2013). "Controlling the reversible thermochromism of polydiacetylene/zinc oxide nanocomposites by varying alkyl chain length." J Colloid and Interface Sci. 389(1):106-114. (Year: 2013).*

Wu, A. et al. (2013). "Thermochromism in Polydiacetylene-ZnO Nanocomposites." J Phys Chem C. 117:19593-19600. (Year: 2013).*

Wu, A. et al. (2014). "Inkjet printing colorimetric controllable and reversible poly-PCDA/ZnO composites." Sensors and Actuators B: Chem. 203:320-326. (Year: 2014).*

* cited by examiner

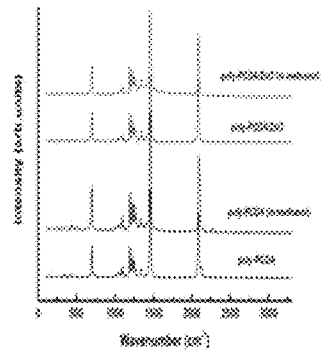 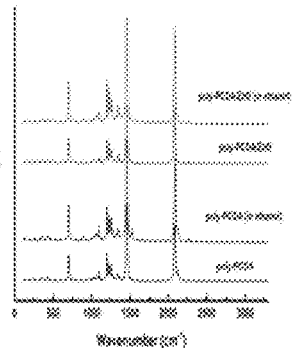 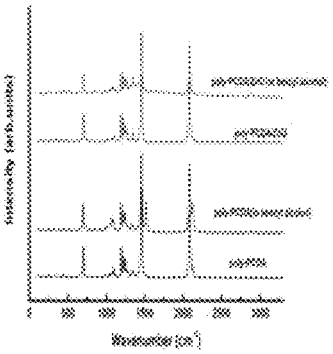
FIG. 4(a)　　　　　FIG. 4(b)　　　　　FIG. 4(c)
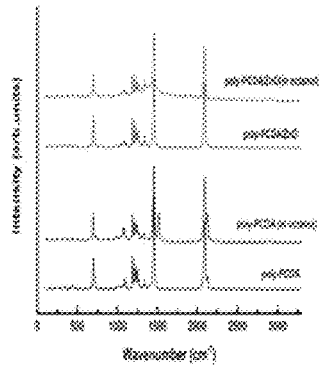 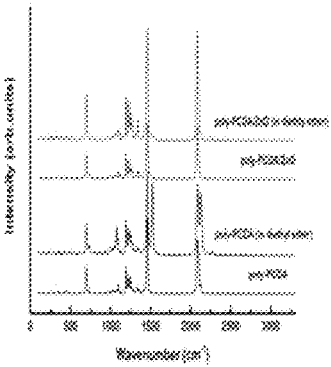 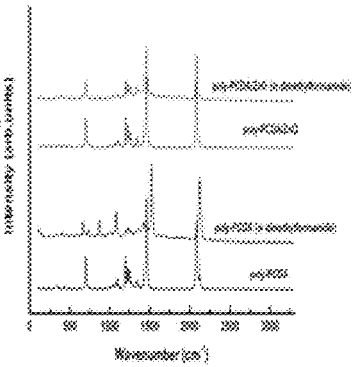
FIG. 4(d)　　　　　FIG. 4(e)　　　　　FIG. 4(f)
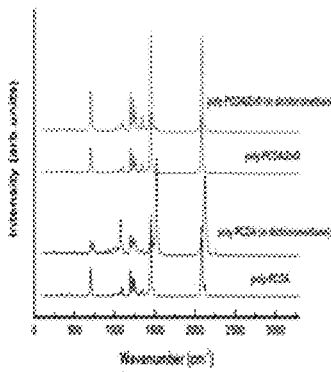 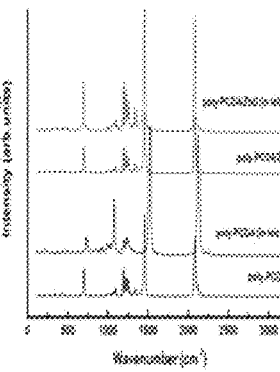 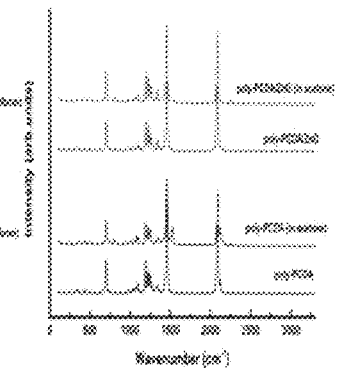
FIG. 4(g)　　　　　FIG. 4(h)　　　　　FIG. 4(i)

FIG. 14(a)
FIG. 14(b)
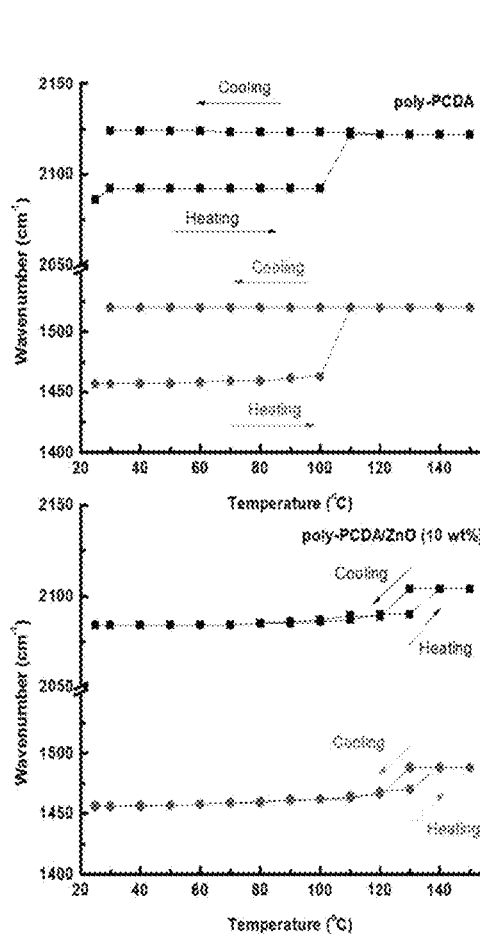
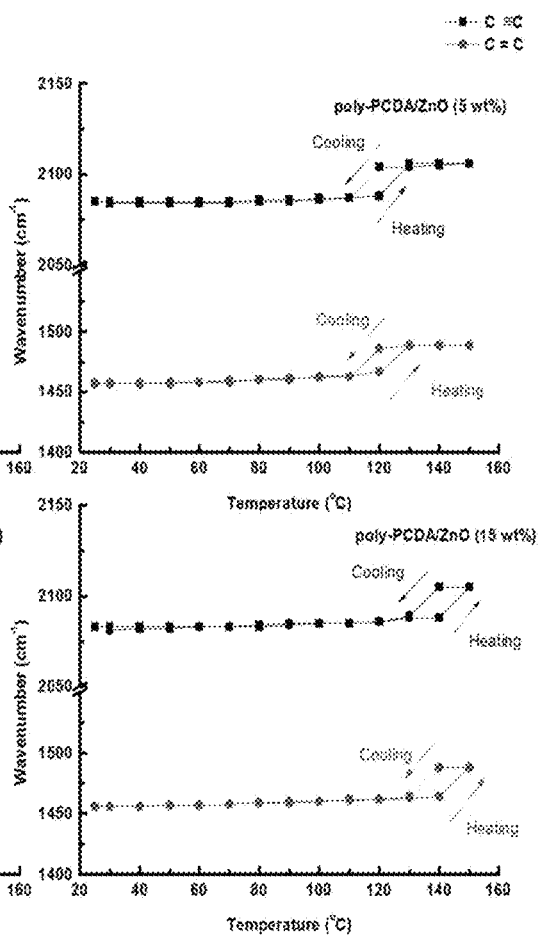
FIG. 14(c)
FIG. 14(d)

5min

10min

15min

20min

25min

US 10,161,876 B2

POLYDIACETYLENE AND POLYDIACETYLENE/ZNO NANOCOMPOSITE SENSORS

CROSS-REFERENCE TO RELATED APPLICATIONS

This application claims the benefit of U.S. Provisional Patent Application Ser. No. 62/044,790 filed Sep. 2, 2014, U.S. Provisional Patent Application Ser. No. 62/044,796 filed Sep. 2, 2014, and U.S. Provisional Patent Application Ser. No. 62/045,322 filed Sep. 3, 2014, the entireties of which are incorporated herein by reference.

FIELD OF THE INVENTION

The present invention relates to the field of polydiacetylenes and in particular to polydiacetylene (PDA) and PDA/ZnO nanocomposite sensors.

BACKGROUND OF THE INVENTION

Materials that change color in response to external stimuli are known as "chromic materials". Such chromic materials may radiate, lose color, or change properties induced by external stimuli. Different stimuli result in different responses in the material being affected.

Inkjet printing processes include several well-known attributes, including providing a non-contact and low cost method of fabrication, the ability to deposit precise amount of materials in a rapid way, the ability to print on specific locations which is controlled by computer, low temperature processing with no need for a vacuum and compatibility with various substrates.

SUMMARY OF THE INVENTION

Polydiacetylenes (PDAs) may be useful as chromatic sensor materials due to their unique blue to red colorimetric transition, which can be triggered by mechanical, temperature and chemical stimuli. The featured chromic transition of PDAs may be either irreversible or reversible depending on chemical structure and interaction of pendant side chains. Strain on the backbone induced by external stimuli leads to red phase formation from blue phase via side chain head group interactions. When strong head group interactions are present in a PDA molecule, the red phase may rapidly reverse back to blue phase upon removal of the stimuli. The irreversible red phase is due to a side chain failing to release the induced strain.

Solid state topotactic photo-polymerization of diacetylene monomers by exposure to UV or γ-radiation makes the synthesis of PDAs more convenient and widespread for use in applications. Recent studies on enhancing the electrical conductivity of PDAs have broadened electrochromic applications of PDAs. However, little attention has been paid to a systematic study of the use of PDAs in chemical sensing.

Research on poly-PCDA/ZnO and poly-TCDA/ZnO nanocomposites has provided a broad understanding of the changes in chromatic properties of the nanocomposites relative to those of the pure polymer. Embodiments disclosed herein include PDAs and PDA/ZnO nanocomposites and phase transitions thereof when exposed to different organic liquids. Raman spectroscopy was used to characterize the PDAs and PDA/ZnO nanocomposites, together with ATR-FTIR studies at ambient temperature and density functional theory simulations to obtain a molecular level understanding of the colorimetric changes. In addition, colorimetric measurements were performed using photographic processing software to quantify the chromatic changes.

Polydiacetylenes (PDAs) and PDA/ZnO nanocomposites based on the monomers: 10,12-pentacosadiynoic acid (PCDA), 10,12-tricosadiynoic acid (TCDA) and 10,12-docosadiynedioic acid (DCDA) monomers, are disclosed in one or more embodiments as chromatic chemical sensing agents for selected organic liquids.

Chromatic sensitivity is associated with the interaction of the organic liquid with the PDA side chain to give rise to the strain-induced blue to red colorimetric transition. Attenuated Total Reflection (ATR)-Fourier Transform Infrared (FTIR) spectroscopy demonstrated that in the PDA/ZnO nanocomposites the PDA side chains form chelates with ZnO. The chromatic properties of PDAs and PDA/ZnO composites in organic liquids, to a certain extent, depend on the side chain length and the number of carboxylic head groups. Pure PDAs and PDA/ZnO nanocomposites in different organic liquids studied by Raman spectroscopy show that the chromatic selectivity of PDAs for certain organic liquids with respect to the blue to red phase transition is closely related to the side chain structure of the PDAs. Moreover, the interactions are stronger with those PDAs where the blue to red transition is irreversible. Density functional theory (DFT) simulations show that the chromatic sensitivity of the PDAs towards a particular organic correlates with the C—C bond torsion angle of the PDA backbone.

In the disclosed PDA/ZnO nanocomposite compositions the PDA component may be present in an amount of 6 to 99.5 weight percent (wt %) based on the total weight of the composition. In one embodiment PDA may be present in an amount of 20 to 99.5 weight percent (wt %) based on the total weight of the composition. In another embodiment PDA may be present in an amount of 50 to 97.5 weight percent (wt %) based on the total weight of the composition. In yet another embodiment PDA may be present in an amount of 85 to 97.5 weight percent (wt %) based on the total weight of the composition.

ZnO may be present in an amount of from 0.5 to 94.0 wt % based on the total weight of the composition. In one embodiment ZnO is present in an amount of from 0.5 to 80.0 wt %. In another embodiment ZnO is present in an amount of from 2.5 to 50.0 wt %. In another embodiment ZnO is present in an amount of from 2.5 to 15.0 wt %. In one embodiment ZnO is present in an amount of from 5.0 to 15.0 wt %. The ZnO is nanoparticle-sized having an average particle size of 0.01-99 nm, more preferably 0.1-99 nm, more preferably 0.1-15 nm.

In one embodiment, compositions including PDA and 2.5 wt % or more of ZnO having a particle size range less than 100 nm are disclosed.

In another embodiment, compositions are disclosed which include PDA and 2.5-15 wt % or more of ZnO having a particle size range less than 100 nm.

In another embodiment, compositions are disclosed which include PDA and 5-15 wt % or more of ZnO having a particle size range less than 100 nm.

In yet a further embodiment compositions are disclosed which consist of PDA and 2.5-15 wt % of ZnO having a particle size range less than 100 nm.

In another embodiment, compositions are disclosed which consist of PDA and 5-15 wt % or more of ZnO having a particle size range less than 100 nm.

In one embodiment novel nanocomposite inks for thin film applications disclosed herein are made by dispersing a precursor PDA monomer in the absence of and/or in the presence of stabilizing agents utilizing aqueous and non-aqueous media as the continuous phase. Desired chromatic transition properties may be attained by changing the ratio of PDA to nanosized ZnO. The chromatic transition properties may be varied according to the particle size of ZnO, stabilizer type and dispersing media.

In still a further embodiment, compositions are disclosed which include a suspension of PDA and 0.5-94 wt % of ZnO having a particle size range below 100 nm. Such suspensions may be applied to substrates using conventional inkjet printing. In a further embodiment an ink composition consists of a suspension of PDA and 2.5-15 wt % of ZnO having a particle size range below 100 nm in chloroform.

The formulated inks may be fit for a variety of inkjet printing processes. For example, in one embodiment the formulated ink is fit for 10 picoliter inkjet printing. The disclosed PDA/ZnO nanocomposites may fulfill completely/partially reversible or irreversible color change responding to chemical stimulus.

In yet a further embodiment PDA/ZnO thin film sensors are disclosed. Film sensors may include PDA and ZnO nanoparticles disposed on a substrate wherein the ZnO nanoparticles have an average particle size of 0.01-99 nm. In one embodiment film sensors are provided which include a substrate and a film consisting of poly-TCDA and ZnO nanoparticles disposed on the substrate wherein the ZnO nanoparticles have an average particle size of 0.01-99 nm. The film sensors may consist of PDA and 0.5-94 wt % of ZnO.

For example, and not by way of limitation, PDA/ZnO nanocomposites such as but not limited to water-based 10,12-pentacosadiynoic acid (PCDA)/ZnO nanocomposites with different concentrations of ZnO nanoparticles may be successfully inkjet printed.

In yet a further embodiment, thermochromically reversible compositions including PCDA and nanosize ZnO having a particle size range less than 100 nm are disclosed. Inkjet printer-fabricated poly-PCDA/ZnO nanocomposites show reversible and stable chromatic properties at corresponding thermochromic transition temperatures. In some embodiments, by varying the concentration of ZnO, the chromatic properties of poly-PCDA/ZnO can be tailored to provide a simple way to apply poly-PCDA/ZnO for chemical and/or thermal sensing applications.

In accordance with a further embodiment a thermochromically reversible composition includes PCDA and from 0.5-94% by weight of ZnO nanoparticles. In some embodiments the composition includes at least 5% by weight of ZnO having a particle size range less than 100 nm. In another embodiment a thermochromically reversible composition is disclosed in the form of a suspension including PCDA and at least 10% by weight of ZnO having a particle size range less than 100 nm. In still another embodiment a thermochromically reversible composition is disclosed in the form of a suspension including PCDA and at least 15% by weight of ZnO having a particle size range less than 100 nm. The compositions may be in the form of a suspension, a liquid, solid, etc.

Compositions disclosed and described herein may be employed as inks for forming chemical or thermal sensors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that those having ordinary skill in the art will have a better understanding of how to make and use the disclosed systems and methods, reference is made to the accompanying figures wherein:

FIGS. 4(a)-4(i) are graphical depictions of Raman spectra of poly-PCDA and poly PCDA/ZnO in the blue phase and in different organic liquids in accordance with one or more embodiments of the present invention;

FIGS. 14(a)-(d) are graphical depictions of the polymer backbone C≡C and C=C stretching mode frequencies of poly-PCDA and poly-PCDA/ZnO composites with different ZnO content on heating and cooling in accordance with one or more embodiments of the present invention;

DETAILED DESCRIPTION OF THE INVENTION

Figure 1:
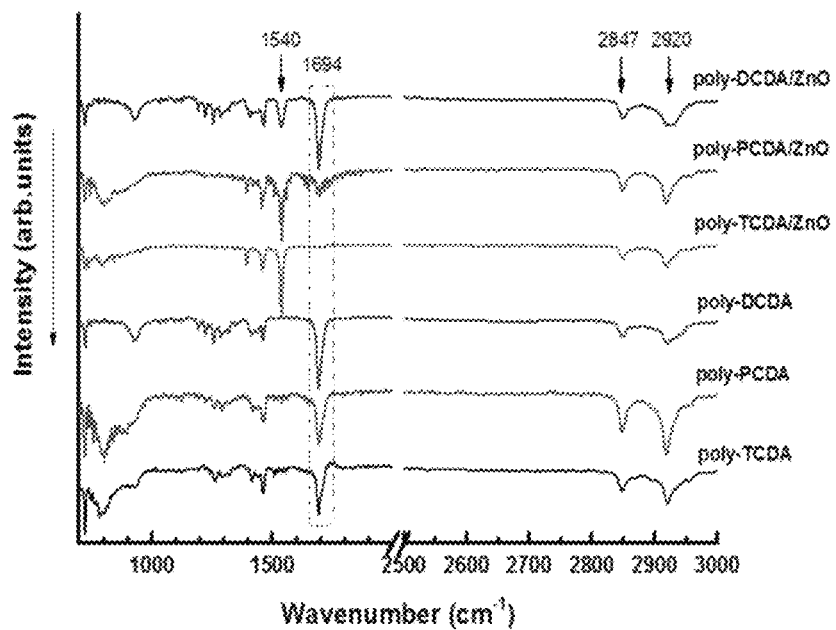
FIG. 1 is a graphical depiction of ATR-FTIR spectra at room temperature in the blue phase of poly-DCDA, poly-PCDA and poly-TCDA, and their corresponding ZnO composites in accordance with one or more embodiments of the present invention.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Compositions disclosed in which the Zn is described as nanosized means and includes Zn particles, having an average particle size of less than 100 nm. Compositions including nanosized Zn are sometimes referred to herein as "nanocomposites".

Polydiacetylenes (PDAs) and PDA/ZnO nanocomposites based on the monomers 10,12-pentacosadiynoic acid (PCDA), 10,12-tricosadiynoic acid (TCDA) and 10,12-docosadiynedioic acid (DCDA) monomers are disclosed in one or more embodiments as chromatic chemical sensing agents for selected organic liquids.

Compositions disclosed herein may be incorporated into the form of an ink, paint, spray or other type of coating for subsequent application and use. Accordingly, any conventional components required for the production of such ink, paint, etc. may be included, such as polymeric binders, plasticizers, UV absorbents, etc.

PDAs, whether PCDA, TCDA or DCDA, may be present in an amount of 6 to 99.5 weight percent (wt %) based on the total weight of the composition. In one embodiment the PDA may be present in an amount of 20 to 99.5 weight percent (wt %) based on the total weight of the composition. In another embodiment the PDA may be present in an amount of 50 to 97.5 weight percent (wt %) based on the total weight of the composition. In yet another embodiment the PDA may be present in an amount of 85 to 97.5 weight percent (wt %) based on the total weight of the composition.

ZnO may be present in an amount of from 0.5 to 94.0 wt % based on the total weight of the composition. In one embodiment ZnO is present in an amount of from 0.5 to 80.0 wt %. In another embodiment ZnO is present in an amount of from 2.5 to 50.0 wt %. In another embodiment ZnO is present in an amount of from 2.5 to 15.0 wt %. In one embodiment ZnO is present in an amount of from 5.0 to 15.0 wt %. The ZnO is nanoparticle-sized having an average particle size of 0.01-99 nm, more preferably 0.1-99 nm, more preferably 0.1-15 nm.

Syntheses of the presently disclosed PDA and nanosized PDA/ZnO compositions were carried out on a laboratory scale. Representative processes for preparation of PDA and PDA/ZnO compositions are disclosed in the examples and experiments hereinbelow.

Examples and Experiments—Chemical Sensing Agents

Materials.

TCDA, PCDA and DCDA were purchased from GFS Chemicals and nanocrystalline ZnO (<100 nm diameter) was purchased from Sigma-Aldrich. Analytical grade chloroform was purchased from Sigma-Aldrich and used without further purification.

Synthesis of PDA/ZnO Nanocomposites.

PDA/ZnO suspensions were prepared by suspending 0.045 mMol equivalent of ZnO in 10 mM solution of the PDA monomer in chloroform. The suspension contained in a beaker was sonicated in a water bath at room temperature for 30 min and dried at 40° C. with magnetic stirring for 8 hours. The magnetic stirring was stopped after the solid state was achieved. The pure PDA monomer and PDA monomer/ZnO composites were polymerized to the blue phase of PDA and PDA/ZnO composite by irradiating with a 254 nm wavelength UV source. Powders of the blue phase composite were obtained by scraping from the beaker and grinding into a fine powder. Red phase composite powders were similarly produced and suspended in different organic liquids.

Raman Spectroscopy.

Raman spectra were obtained using a Mesophotonics Raman spectrometer with 785 nm laser excitation. The spectrometer was calibrated using a silicon wafer and diamond powder standards to a frequency accuracy of 1 cm$^{-1}$. Thick films for the Raman measurements were prepared by mixing suspensions of PDA monomer with ZnO, using chloroform as the suspension medium. After drying and 254 nm uv-irradiation, Raman spectra from the dry powders of PDA and PDA/ZnO were measured on a silicon wafer. The effect of organic liquids on the PDAs were carried out by suspending the same molar amounts of PDA or PDA/ZnO in 4 ml of the organic liquid, and measuring the Raman spectra after 5 minutes of bath sonication of the suspension.

ATR-FTIR Spectroscopy.

Attenuated Total Reflection (ATR)-Fourier Transform Infrared (FTIR) was carried out using a Nicolet Thermo-Electron FTIR 560 spectrometer with a MIRacle attenuated total reflectance (ATR) platform assembly and a Ge plate.

RGB Measurements of Poly-PCDA and Poly-PCDA/ZnO at Different Temperatures.

The "red phase" and "blue phase" defined by Raman spectroscopy are based on the vibration modes of molecular structures of PDAs, which means, especially in the blue phase and red phase coexisting system, Raman spectra could not tell the exact overall color as the one detected by human eye. Thus, for precise colorimetric information, the photographic images of PDAs or PDA/ZnO composites in an organic liquid were quantitatively analyzed by photographic processing software to obtain the RGB values obtained from the combination of red, green and blue colors.

ATR-FTIR Spectroscopy.

ATR-FTIR can provide information on chemical interactions between the PDA side chain in poly-PCDA/ZnO and poly-TCDA/ZnO. To confirm if poly-DCDA/ZnO shows similar behavior, FTIR spectroscopy was carried out on this nanocomposite and also, for comparison, on poly-PCDA/ZnO and poly-TCDA/ZnO. The effect of the side chain head group and ZnO interaction is reflected in the FTIR spectra shown in FIG. 1. In the 700-3000 cm$^{-1}$ spectral region, lines at 2920 and 2847 cm$^{-1}$ can be assigned to the asymmetric and symmetric stretching vibrations, respectively, of the $CH_2$ groups on the side chains, the lines at 1463 and 1417 cm$^{-1}$ can be assigned to $CH_2$ scissoring modes, and the line at 1694 cm$^{-1}$ can be attributed to the hydrogen-bonded carbonyl C=O stretching vibration. A relatively strong line appears at 1540 cm$^{-1}$ in the spectra of PDA/ZnO composites together with a concomitant decrease in intensity of the C=O stretching line at 1694 cm$^{-1}$. This 1540 cm$^{-1}$ line can be assigned to an asymmetric COO stretching vibration and its presence in the spectra together with the corresponding decrease in the intensity of the C=O stretching line can be attributed to the formation of a chelate between neighboring side chain —COOH head groups of the PDAs and $Zn^{2+}$ ions from ZnO. However, comparing different PDA/ZnO composites under the same stoichiometric ratio of PDA to ZnO, even though chelate formation between PDA and ZnO are indicated in the ATR-FTIR spectra, the C=O line at 1694 cm$^{-1}$ decreases in intensity to different degrees. For example, there is no evidence of the C=O line in the FTIR spectrum of poly-TCDA/ZnO. Also, the C=O line is very weak in poly-PCDA/ZnO, but remains relatively strong in poly-DCDA/ZnO (FIG. 1). This suggests that chelation occurs only at one —COOH head group in poly-DCDA/ZnO, and at the one available —COOH head group present in both poly-TCDA and poly-PCDA.

Raman Scattering.

Figure 2:
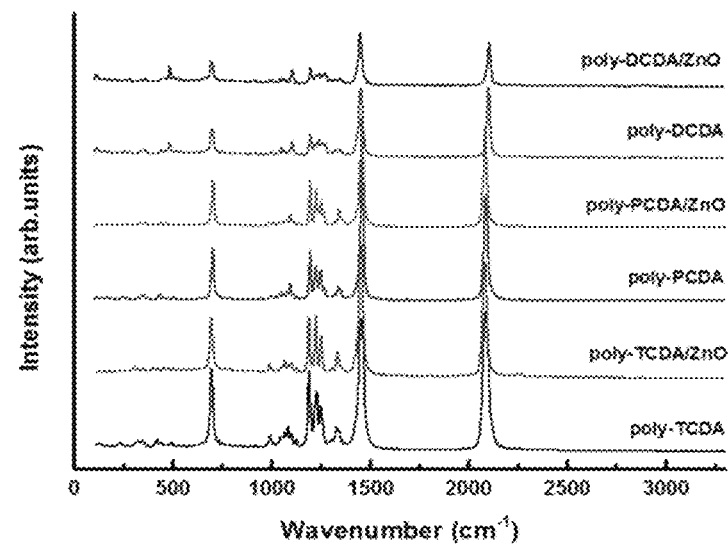
FIG. 2 is a graphical depiction of Raman spectra of poly-DCDA, poly-PCDA and poly-TCDA, and their corresponding ZnO nanocomposites in the blue phase at room temperature in accordance with one or more embodiments of the present invention.
Figure 3A:
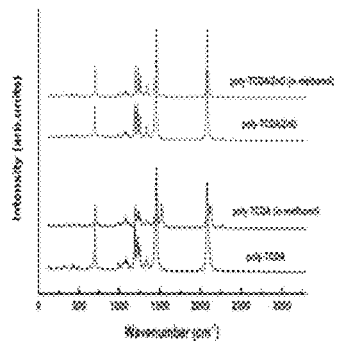
FIGS. 3(a)-3(i) are graphical depictions of Raman spectra of poly-TCDA and poly TCDA/ZnO in the blue phase and in different organic liquids in accordance with one or more embodiments of the present invention.
Figure 3B:
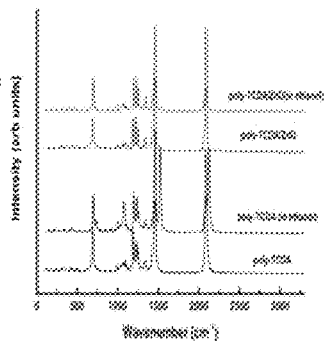
Figure 3C:
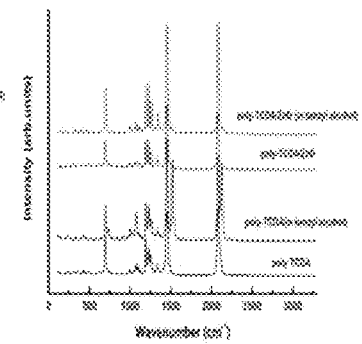
Figure 3D:
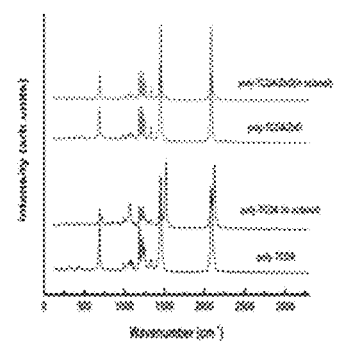
Figure 3E:
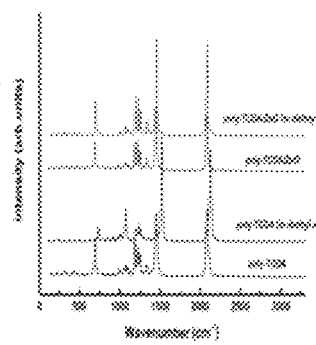
Figure 3F:
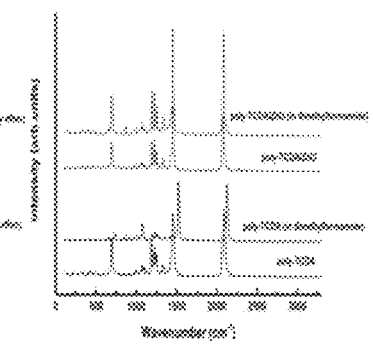
Figure 3G:
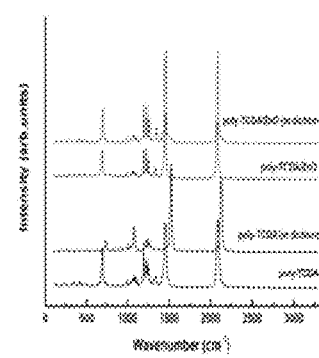
Figure 3H:
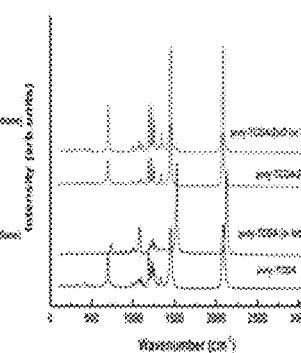
Figure 3I:
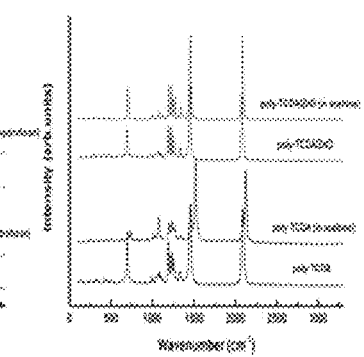
Figure 5A:
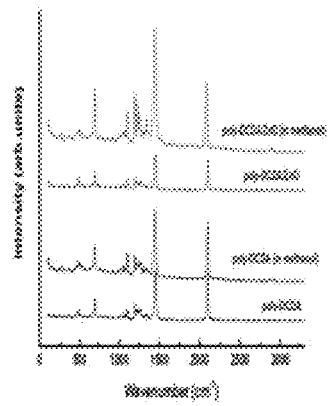
FIGS. 5(a)-5(i) are graphical depictions of Raman spectra of poly-DCDA and poly DCDA/ZnO in the blue phase and in different organic liquids in accordance with one or more embodiments of the present invention.
Figure 5B:
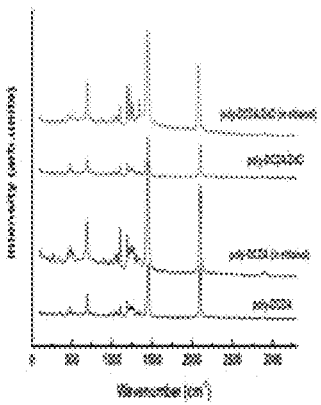
Figure 5C:
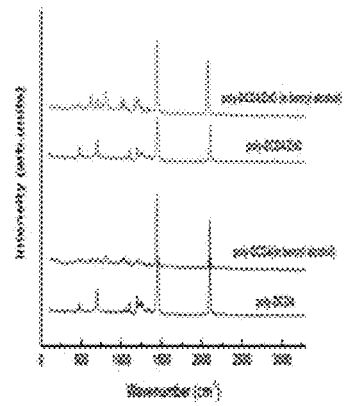
Figure 5D:
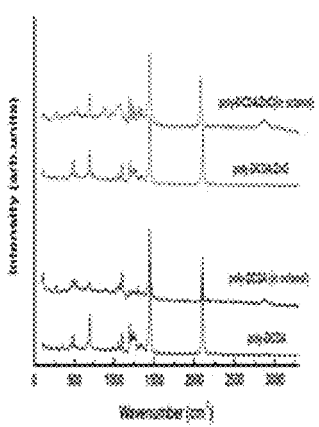
Figure 5E:
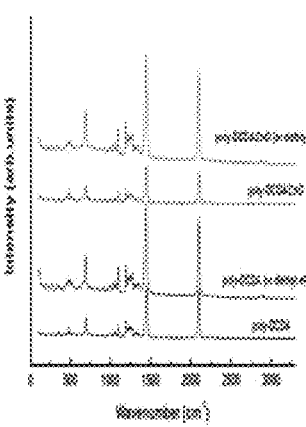
Figure 5F:
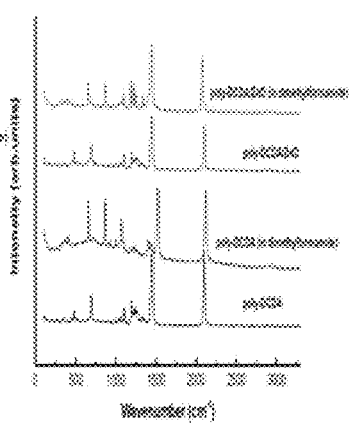
Figure 5G:
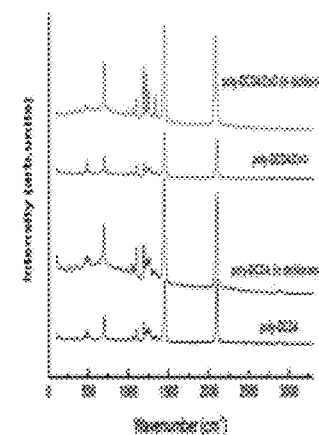
Figure 5H:
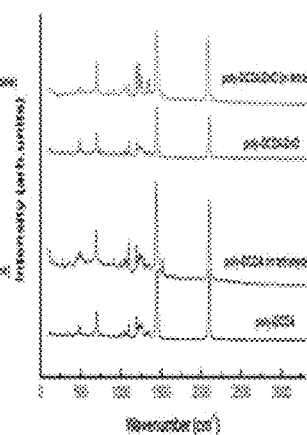
Figure 5I:
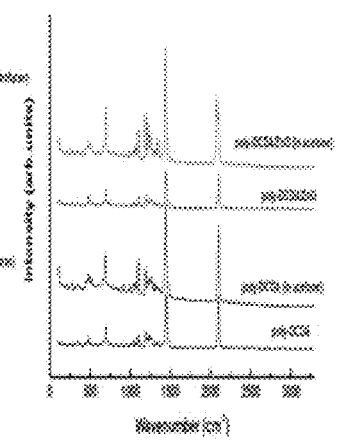

Raman scattering due to the molecular vibrational modes of the conjugated polymer backbone are expected to be primarily resonance-enhanced for excitation using 780 nm laser radiation. From the Raman spectra in FIG. 2 for the pure PDAs in the blue phase, two intense lines near 2100 cm$^{-1}$ and 1450 cm$^{-1}$ are observed at room temperature in the blue phase, which can be definitively assigned to the C≡C and C=C stretching modes of the polymer backbone, respectively. However, there are small but measurable differences in the C≡C and C=C stretching mode frequencies for the different PDAs as summarized in Table 1.

TABLE 1

Polymer backbone Raman frequencies for different PDAs and corresponding PDA/ZnO nanocomposites in the blue phase in the presence of organic liquids.

| Organic liquid | Frequencies (cm$^{-1}$) | | | | | |
|---|---|---|---|---|---|---|
| | C=C | C≡C | C=C | C≡C | C=C | C≡C |
| | poly-TCDA | | poly-PCDA | | poly-DCDA | |
| none | 1456 | 2084 | 1457 | 2086/2124* | 1452 | 2102 |
| methanol | 1458/1524 | 2084/2124 | 1457 | 2096/2124* | 1446 | 2102 |
| ethanol | 1456/1524 | 2084/2124 | 1457/1522* | 2090/2124* | 1446 | 2102 |
| benzyl alcohol | 1456/1522 | 2082/2124 | 1457/1522 | 2086/2124* | 1442 | 2098 |
| octanol | 1454/1518 | 2080/2120 | 1457/1522 | 2086/2122* | 1444 | 2100 |
| diethyl ether | 1522/1456* | 2126/2084* | 1457/1522 | 2086/2124 | 1444 | 2100 |
| DMF | 1524 | 2124 | 1457*/1522 | 2086*/2126 | 1522/1444* | 2120 |
| DCM | 1522 | 2126 | 1457/1520 | 2086/2126 | 1444 | 2100 |
| THF | 1522 | 2124 | 1524 | 2124 | 1520*/1446 | 2120*/2102 |
| acetone | 1524/1458 | 2126/2082 | 1457/1522 | 2090/2122* | 1444 | 2102 |
| | poly-TCDA/ZnO | | poly-PCDA/ZnO | | poly-DCDA/ZnO | |
| none | 1454 | 2082 | 1456 | 2084 | 1448 | 2104 |
| methanol | 1458/1524* | 2084/2118* | 1456 | 2084 | 1446 | 2084/2104* |

TABLE 1-continued

Polymer backbone Raman frequencies for different PDAs and
corresponding PDA/ZnO nanocomposites in the blue phase in the presence of organic liquids.

| Organic liquid | Frequencies (cm$^{-1}$) | | | | | |
|---|---|---|---|---|---|---|
| | C=C | C≡C | C=C | C≡C | C=C | C≡C |
| ethanol | 1458/1524* | 2086/2122* | 1456/1522* | 2084/2124* | 1446 | 2080/2104* |
| benzyl alcohol | 1458/1522* | 2086/2124* | 1456/1522* | 2084 | 1444 | 2078 |
| octanol | 1454/1518* | 2082/2118* | 1456 | 2084 | 1446 | 2078 |
| diethyl ether | 1458/1522* | 2086/2124* | 1456/1522* | 2084/2124* | 1444 | 2100 |
| DMF | 1456/1520* | 2082/2124* | 1456/1522* | 2084/2126* | 1444 | 2076 |
| DCM | 1458/1522* | 2086/2126* | 1456/1520* | 2086/2126* | 1446 | 2080/2104* |
| THF | 1456/1522* | 2084/2118* | 1456/1524* | 2084/2124* | 1446 | 2080 |
| acetone | 1456/1524* | 2084/2124* | 1456/1522* | 2084/2122* | 1444 | 2080/2104* |

"*" represents a shoulder, DMF—dimethylformamide, DCM—dichloromethane, and THF—tetrahydrofuran The C=C stretching mode frequencies for poly-TCDA and poly-PCDA are essentially the same within ±1 cm$^{-1}$, whereas the C≡C stretching mode frequencies shows a small 2 cm$^{-1}$ upshift and the appearance of a shoulder at 2124 cm$^{-1}$ in poly-PCDA that is most likely due to the presence of a red phase impurity in the sample. The CC stretching mode frequency in poly-DCDA is, however, 16 and 18 cm$^{-1}$ higher than that for poly-PCDA and poly-TCDA, respectively, indicating a higher strain on the polymer backbone in poly-DCDA associated with the presence of two —COOH head groups on its side chains. Chelate formation between PDA and ZnO in poly-TCDA/ZnO and poly-PCDA/ZnO results in a small frequency downshift for both the C≡C and C=C stretching modes relative to that of the pure polymer due to a small decrease in strain on the polymer backbone. By contrast, in poly-DCDA/ZnO there is a 4 cm$^{-1}$ downshift in the C=C stretching mode frequency but a 2 cm$^{-1}$ upshift in the C≡C stretching mode frequency, probably linked to the presence of two —COOH head groups in poly-DCDA.

In order to evaluate the use of the PDAs and PDA/ZnO nanocomposites as chromatic chemical sensors, Raman spectroscopy was carried out to study the effect of organic liquids on the Raman spectra of the PDAs and PDA/ZnO nanocomposites. Methanol, ethanol, benzyl alcohol, octanol, diethyl ether, dimethylformamide (DMF), dichloromethane (DCM), tetrahydrofuran (THF) and acetone (analytical grade from Sigma-Aldrich) were selected as organic liquids to trigger a color change. The results are shown in FIGS. 3(a)-5(i), and the observed C=C and C≡C stretching mode frequencies of the PDAs in the organic liquids are listed in Table 1.

With reference to FIGS. 3(a)-3(i), it is evident that the C≡C and C=C stretching mode lines of poly-TCDA and poly-TCDA-ZnO are either split by the appearance of a line at higher frequency due to the partial conversion to the red phase or shift to higher frequencies due to complete conversion to the red phase, depending on the organic liquid added. Poly-TCDA showed a peak splitting in the C≡C and C=C stretching mode regions of the Raman spectrum due to partial formation of the red phase when alcohols and acetone are present, while in DMF, DCM and THF, the C≡C and C=C Raman peaks increase in frequency to new values due to complete conversion of the blue to the red phase. In the presence of diethyl ether a small shoulder due to the blue phase remains at a lower frequency although conversion to the red phase is complete. For poly-TCDA/ZnO, only a high frequency shoulder is formed in the presence of all the selected organic liquids, indicating that conversion to the red phase is not complete. The unchanged blue phase is likely to be due to chelate formation between neighboring side chains in the nanocomposites which could stand up with the chemical stimuli.

With reference to FIGS. 4(a)-4(i), the behavior of the Raman spectra of blue poly-PCDA and poly-PCDA/ZnO nanocomposite in different organic liquids is similar to that of poly-TCDA and its corresponding ZnO nanocomposite, except for the absence of red phase formation in methanol. For the other three alcohols, only weak red phase lines are observed.

Now referring to FIGS. 5(a)-5(i), in contrast to the results of poly-TCDA and poly-PCDA, poly-DCDA shows a small downshift in the C=C stretching mode frequency in the presence of organic liquids possibly due to chemical interaction with the organic liquids (except in DMF and THF). For the C≡C stretching mode, the upshift due to red phase formation is only observed in DMF and THF, while in most other liquids, the C≡C stretching mode frequency either remains the same (as in methanol, ethanol and acetone) or downshifts slightly (as in benzyl alcohol, octanol, diethyl ether and DCM). Compared with poly-DCDA, the downshift of the C≡C peak frequencies for poly-DCDA/ZnO is much larger in the presence of the organic liquids (for example from 2104 cm$^{-1}$ to about 2080 cm$^{-1}$), whereas the C=C peak frequency downshift is small (from 1448 cm$^{-1}$ to about 1445 cm$^{-1}$).

Figure 6:
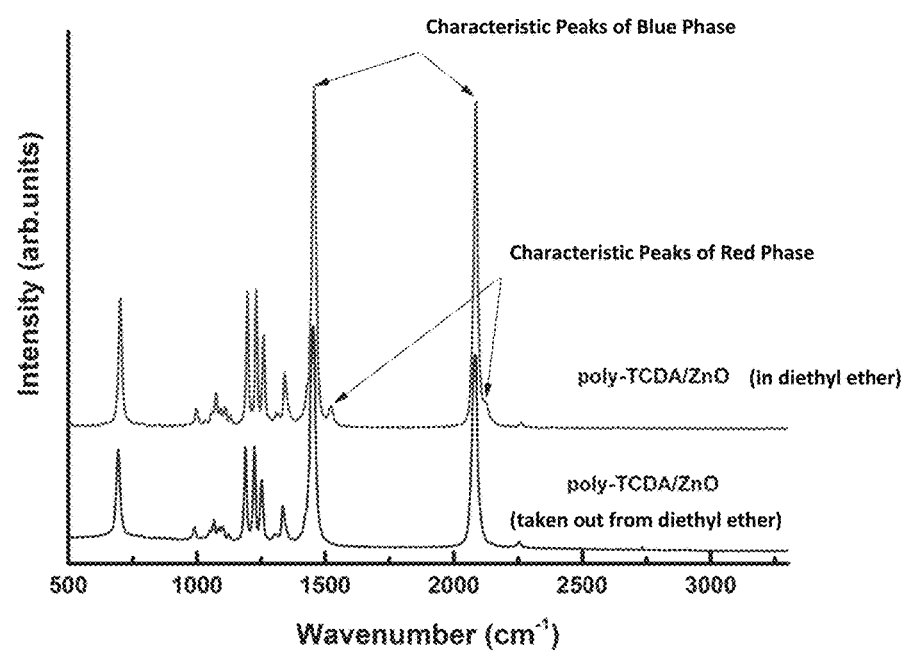
FIG. 6 is a graphical depiction of Raman spectra of poly-TCDA/ZnO (in diethyl ether and taken out from diethyl ether) in accordance with one or more embodiments of the present invention.

Referring to FIG. 6, an important feature worth noting is that the blue to red transition of PDAs induced by the organic liquids are all irreversible, but the organic liquid-induced red phase for all three PDA/ZnO nanocomposites are reversible, the red phase peaks appear in organic liquid environment, and once the PCDA/ZnO composites are taken out from the organic liquid, only characteristic peaks of blue phase could be found in the spectra. This can be attributed to strong chelation interactions comparable to chemical bonding in the PDA/ZnO nanocomposites that provides greater stability to the blue relative to the red phase.

Density Functional Theory Simulations.

Density functional theory (DFT) simulations were carried out to understand the interesting chemical sensing behaviors of the PDAs and PDA/ZnO composites in terms of their molecular structure properties. The simulations were carried out using Material Studio 4.3 (Accelrys Software Inc.) with B3LYP (DND basis set) function in DMol3 modules which is a counterpart of the 6-31 G*basis set of Gaussian 3.0. On balancing between the accuracy and number of computations needed, a medium-accuracy level calculation was selected for the simulations.

Figure 7A:
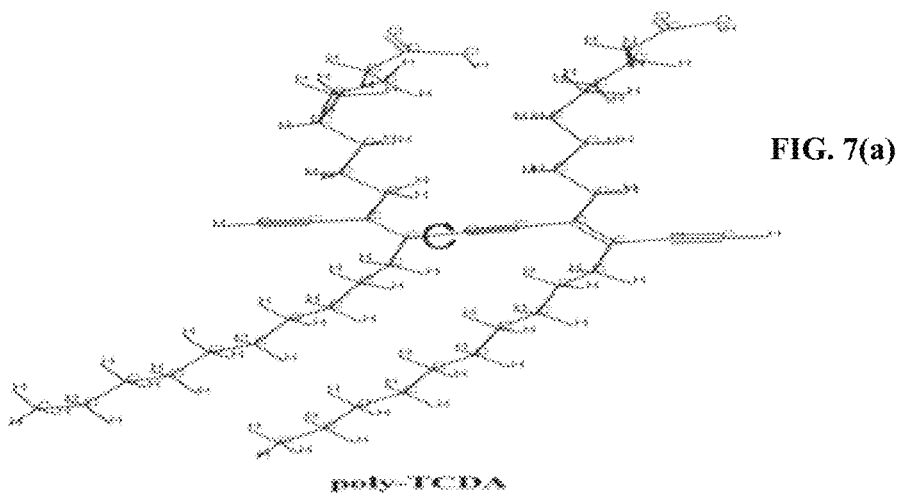
FIGS. 7(a)-(c) are structural depictions of simulated PDA segments: (a) Poly-TCDA, (b) poly-PCDA, and (c) poly-DCDA in accordance with one or more embodiments of the present invention.
Figure 7B:
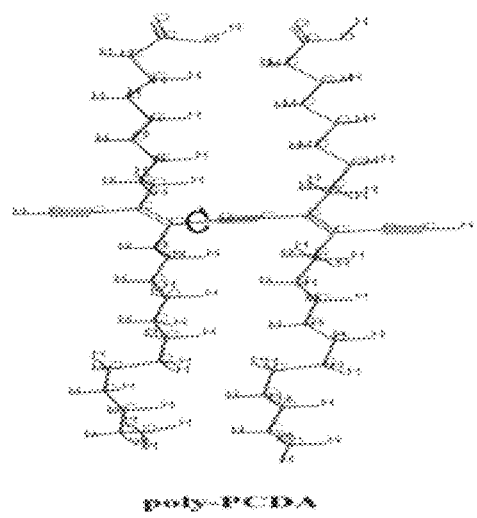
Figure 7C:
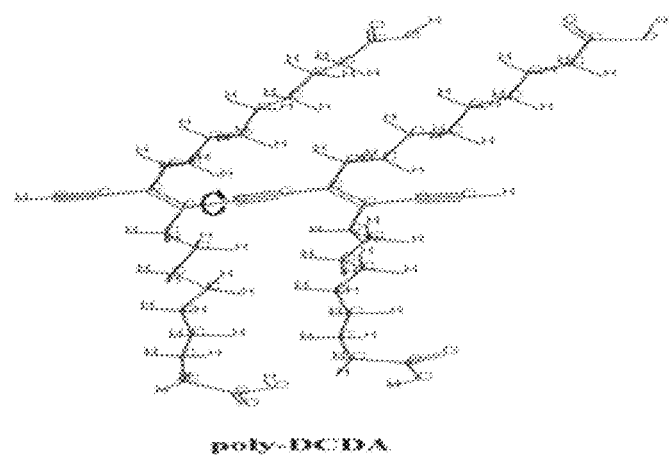
Figure 8:
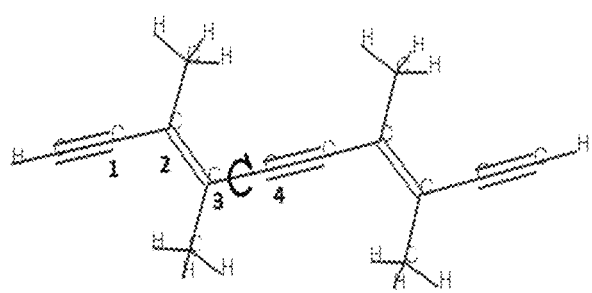
FIG. 8 is a depiction of a structure of the PDA segment used for a C—C torsion angle study conducted in accordance with one or more embodiments of the present invention.

For construction of the molecular structure, consideration was given to the amount of computation needed and limitation of the Linux cluster available to carry out the simulations. Segments of the polymers shown in FIGS. 7(a)-(c), which are equivalent to molecules with a polymerization degree of 2, were used for this simulation. The main difference between the PDAs is the torsion angle of the single bond on the polymer backbone as indicated in FIG. 8. This is probably due to the fact that the backbone carbon chain of the PDAs is in the zig-zag conformation with the possibility that torsion occurs on the carbon-carbon single bond. In order to clearly show the torsion angle of the carbon single bond for different PDAs, a cis-structured backbone is set as the 0° reference point. Also, each PDA was constructed and simulated 5 times to make sure that the conformation of the side chains is in a random state. The results showed that the C—C bond torsion angles surprisingly fall within a certain small range from about 48° to 50° for TCDA, about 38° to 40° for PCDA and about 7° to 8° for DCDA as shown in Table 2.

TABLE 2

C—C torsion angle on the PDA backbones.

| | C—C Torsion Angle (°) | | |
|---|---|---|---|
| Trial Number | poly-TCDA | poly-PCDA | poly-DCDA |
| 1 | 49.018 | 39.746 | 7.561 |
| 2 | 48.176 | 39.862 | 8.012 |
| 3 | 49.694 | 40.354 | 7.402 |
| 4 | 50.402 | 38.708 | 6.986 |
| 5 | 48.464 | 39.454 | 7.124 |

Due to the coincidence of C—C torsion angles in the simulations, it is obvious that the backbone structure of the PDAs is closely related to that of the side chain. In order to investigate the torsion on the backbone, the structure as shown in FIG. 8 was adopted using a methyl group instead of the side chain. The basic idea was to determine how the torsion of the C—C bond affects the backbone structure; therefore, in this simulation the potential energy of this structure was considered as the criterion to evaluate the C—C bond torsion. The trans-structure was set as a reference potential energy point and the potential energy was calculated with the B3LYP/6-31 G*function using C3-C4 torsions angles of 30°, 60°, 90°, 120°, 150° and 180° while other C—C torsion angles were restricted.

Figure 9:
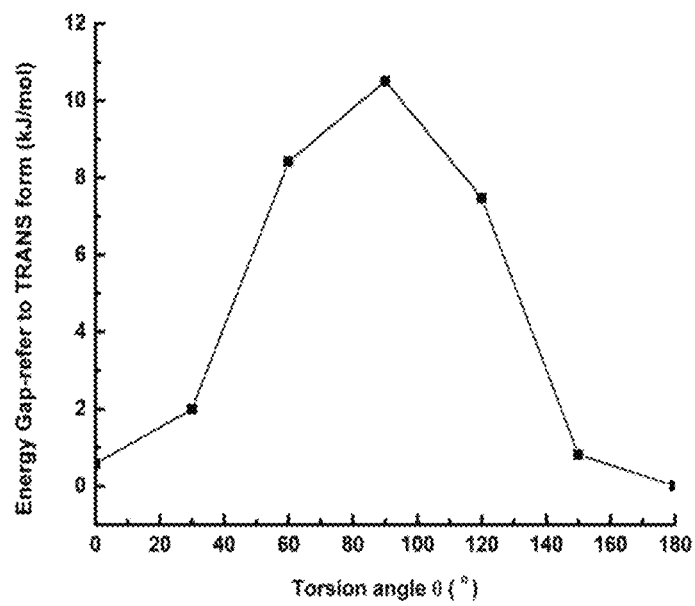
FIG. 9 is a graphical depiction of a potential energy curve as a function of torsion angle around the central C—C bond in cis-carbon with reoptimization of other geometrical parameters in accordance with one or more embodiments of the present invention.

The results of the potential energy calculation are plotted in FIG. 9, which shows that the maximum energy refers to a cis-structure which appears when θ=90°. This plot generally demonstrates how the C—C bond torsion angle affects the backbone system. It can also explain how PDAs with different side chains would exhibit different chromatic and spectroscopic changes discussed above (also see RGB section below). For example, the longer the C—C bond, the less stress is needed to induce a chromatic transition in the PDA, which is consistent with the fact that poly-TCDA is the most chromatically sensitive to the organic liquids evaluated.

RGB Measurements.

Figure 10A:
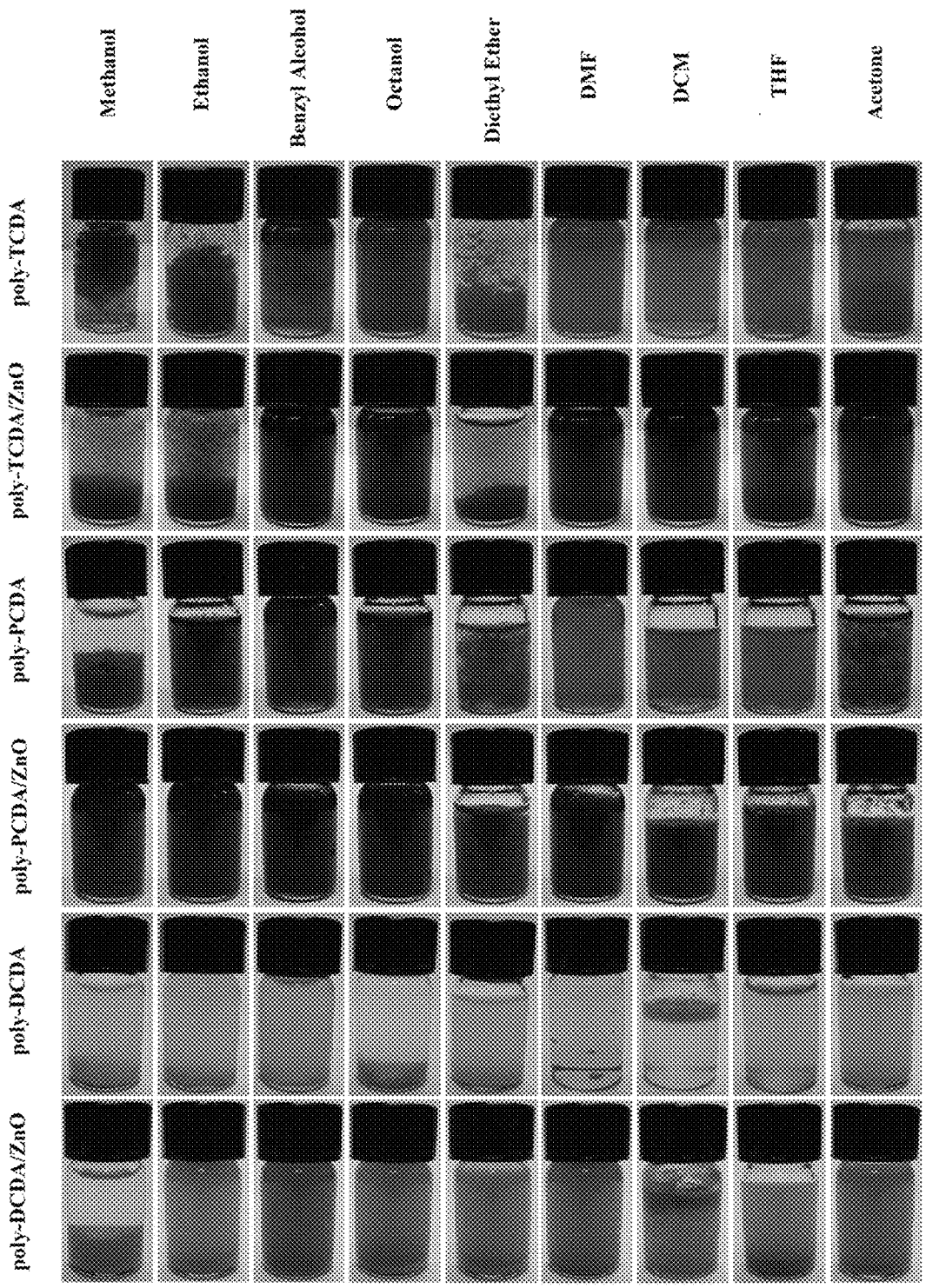
FIG. 10(a) is an array of cropped photographic images of PDAs and PDA/ZnO nanocomposites in selected organic liquids in accordance with one or more embodiments of the present invention.
Figure 10B:
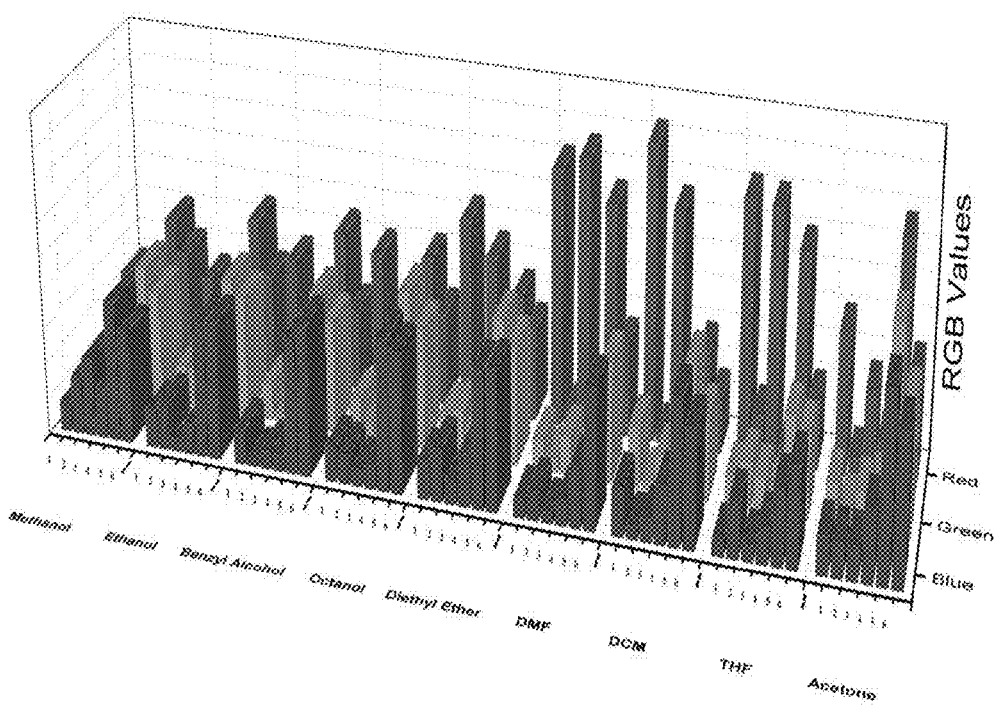
FIG. 10(b) is a graphical depiction of RGB values of the photographic images of FIG. 10(a) analyzed by software in accordance with one or more embodiments of the present invention.

To demonstrate the selective sensing capabilities of the PDAs which could be detected by human eye, RGB measurements were conducted to quantitatively evaluate the color of the PDAs and PDA/ZnO composites in the presence of selected organic liquids. Now referring to FIGS. 10(a) and (b), poly-TCDA turned red on contacting an organic liquid corresponding to a higher red value than green and blue values. Similar phenomena were observed for poly-PCDA samples (except in methanol). However, poly-DCDA only shows a distinguishable red value when DMF and THF are present, indicating that the chemical recognition ability of PDAs is closely related to the chemical structure of the side chains on the PDA backbone.

It was also observed that all the PDA/ZnO nanocomposites show similar RGB values with different degrees of blue color in the presence of different organic liquids. This indicates that the chelates formed in PDA/ZnO nanocomposites involve a strong chemical bond, and can therefore withstand chemical stress to maintain the blue phase (as shown by the Raman data) in the presence of the selected organic liquids.

In accordance with one or more embodiments of the present invention, PDAs based on the monomers 10,12-pentacosadiynoic acid (PCDA), 10,12-tricosadiynoic acid (TCDA) and 10,12-docosadiynedioic acid (DCDA), and their nanocomposites with ZnO are suitable chemical sensors for selected organic liquids. Chromatic sensitivity evaluated by Raman spectral data and quantitative RGB analyses were found to be associated with the interaction of the organic liquids with the PDA side chain to give rise to the blue to red colorimetric transition. ATR-FTIR spectral data show that chelate formation occurs only on one of the two carboxylic head groups in poly-DCDA/ZnO. Due to strong chemical interactions between zinc and carboxylic ions during chelate formation that stabilize the blue phase, chromatic sensitivity to organic liquids is low for PDA/ZnO nanocomposites. Density functional theory (DFT) simulations indicate that the chromatic sensitivity of the PDAs to a particular organic depends on the C—C bond torsion angle of the PDA backbone.

Novel PCDA and PCDA/ZnO Nanocomposite Compositions

In accordance with further embodiments, thermochromically reversible compositions including PCDA and nanosize ZnO having a particle size range less than 100 nm are disclosed. The nanosized ZnO is preferably unalloyed.

Compositions disclosed herein may be incorporated into the form of an ink, paint, spray or other type of coating for subsequent application and use. Accordingly, any conventional components required for the production of such ink, paint, etc. may be included, such as polymeric binders, plasticizers, UV absorbents, etc.

The presently disclosed PCDA/ZnO nanocomposites are novel, as are their uses as chromatic sensors and production thereof using inkjet printing. The functionality of the disclosed PCDA/ZnO nanocomposites may be varied. For example, by changing the ratio of PCDA to ZnO, the chromatic transition temperature may be varied.

Examples and Experiments—Thermochromically Reversible Compositions of PCDA and PCDA/Nanosize ZnO Materials.

PCDA was purchased from GFS Chemicals and nanocrystalline ZnO (<100 nm diameter) was purchased from Sigma-Aldrich. Analytical grade chloroform was purchased from Sigma-Aldrich and used without further purification.

Preparation of PCDA and PCDA/ZnO Composites Ink.

Different amounts of ZnO (5 wt %, 10 wt %, 15 wt %) were suspended in a solution of the PCDA monomer (4 mM) in chloroform. The suspension was sonicated in a water bath at 25° C. for 30 min and dried at 40° C. with magnetic stirring for 8 hours. The magnetic stirring was stopped after the chloroform evaporated. PCDA or PCDA/ZnO nanocomposite ink was prepared by probe sonicating 1 mMol PCDA or PCDA/ZnO in 40 ml deionized water (DI water) with a certain amount (1.5 wt %) of sodium dodecyl sulfate (SDS) for 30 min. A constant temperature bath at 25° C. was utilized to prevent heating during sonication.

Fabrication of Poly-PCDA and Poly-PCDA/ZnO Composites by Inkjet Printing.

The design and fabrication the poly-PCDA based sensor was conducted using a Fujifilm Dimatix printer (Model DMP-2800), which is based on piezoelectric inkjet technology. The cartridge with a nozzle pore size of ca. 20 µm in diameter was filled with water-based PCDA or PCDA/ZnO suspension, which was printed on unmodified A4-sized paper. Both PCDA and PCDA/ZnO were inkjet printed with 25 volts applied on nozzle pores. Nozzle cleaning was carried after every 5 bands of printing and the platen temperature was maintained at 40° C. to evaporate the water. After inkjet printing either monomeric PCDA or PCDA/ZnO composite suspensions on flexible substrates, the printed images were formed by irradiating with a 254 nm wavelength UV source following solvent evaporation at 40° C. The patterns for Raman and optical densitometry measurements were in 5 mm×5 mm square shape.

Material Characterization, Instrumentation and Methods.

A Mesophotonics Raman spectrometer with 785 nm laser excitation was used to collect the Raman spectra at room temperature. Temperature-dependent Raman measurements were carried out with an EZRaman LE Raman Analyzer system from Optronics using 785 nm laser excitation coupled to a Leica optical microscope. The spectrometer was calibrated using silicon wafer and diamond powder standards to a frequency accuracy of 1 $cm^{-1}$. The variable temperature optical stage used is from Linkam Scientific Instruments Ltd. Thin films for the Raman measurements were prepared by S-layer inkjet printing the water-based PCDA or PCDA/ZnO suspension on a silicon wafer. After 254 nm uv-radiation, the polymerized PCDA and poly-PCDA/ZnO were measured directly.

Fourier Transform Infrared (FTIR) was carried out using a Nicolet ThermoElectron FTIR 560 spectrometer together with a MIRacle attenuated total reflectance (ATR) platform assembly and a Ge plate. Poly-PCDA/composites powder was obtained by scratching off the inkjet printed poly-PCDA/composites on a Kapton film. The inkjet printing parameters on Kapton were the same as that for inkjet printing on paper substrates As a quantitative measure of the vividness or dullness of a color (or how close the color is to either the gray or pure hue), chromaticity of thin film and coated samples at different temperatures during the heating process was measured directly by an X-Rite 518 optical densitometer on a temperature-controlled hot plate. For precise colorimetric information, the photographic images of PDAs or PDA/ZnO composites were also quantitatively analyzed by photographic processing software to obtain the RGB values obtained from the combination of red, green and blue colors.

Scanning electron microscope (SEM) images were obtained with a VP-1530 Carl Zeiss LEO (Carl Zeiss, Peabody, Mass., USA) field-emission SEM. The samples were mounted on aluminum stubs using double-sided carbon tape. Particle sizes were determined using SEM images with scale-based ImageJ software, which defines the length of each pixel and selects a region to calculate the statistical particle size.

Inkjet Printing of PCDA and PCDA/ZnO.

Inkjet printing was conducted by using Fujifilm Dimatix (Model 2800) inkjet printer. Due to the facts that the nozzles of s 10-picoliter printing cartridge are ca. 20 µm in diameter and the PCDA/ZnO composite inks are water based suspensions, sonication power and duration will be the primary factors that affect the feasibility of inkjet printing these materials.

Figure 18A:
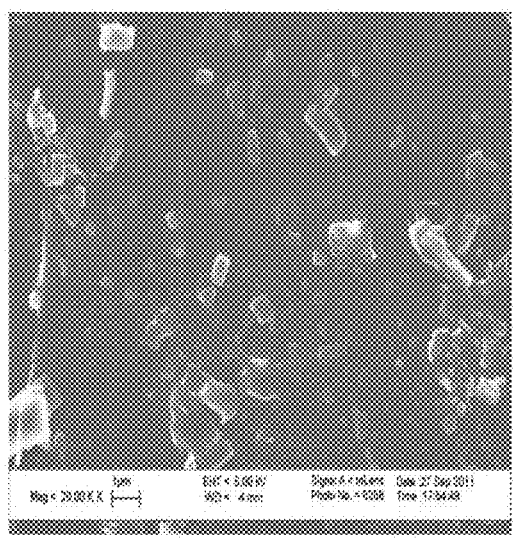
FIGS. 18(a)-(b) are SEM images of PCDA after horn sonication (left) and bath sonication (right) in accordance with one or more embodiments of the present invention.
Figure 18B:
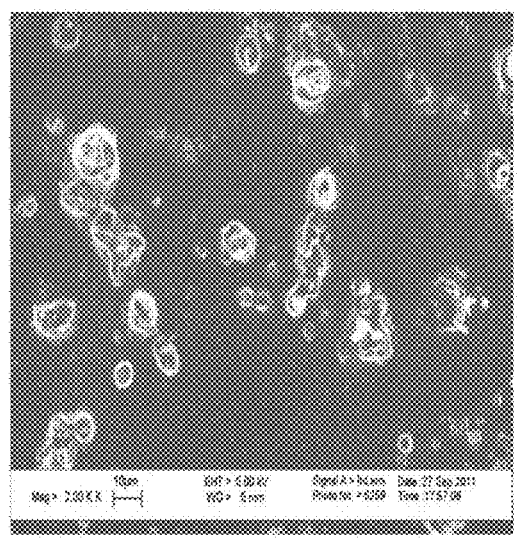
Figure 19A:
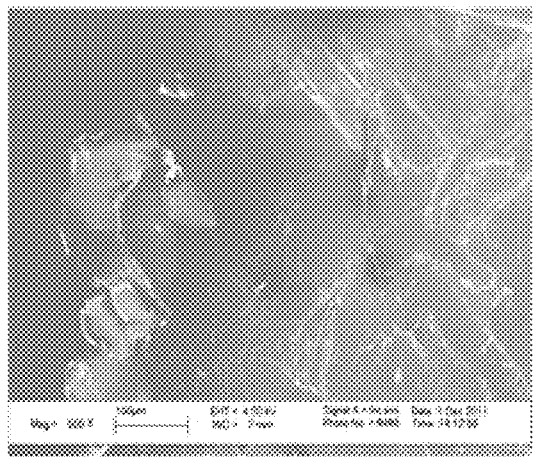
FIGS. 19(a)-(e) are SEM images of PCDA after different probe sonication durations in accordance with one or more embodiments of the present invention.
Figure 19B:
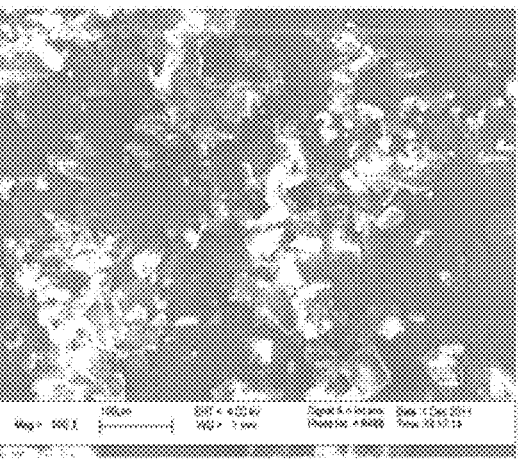
Figure 19C:
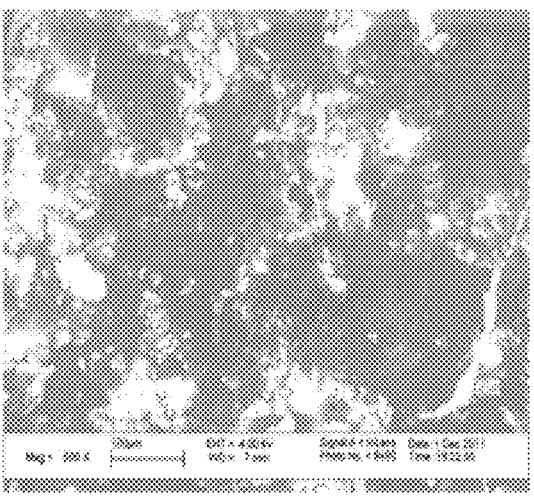
Figure 19D:
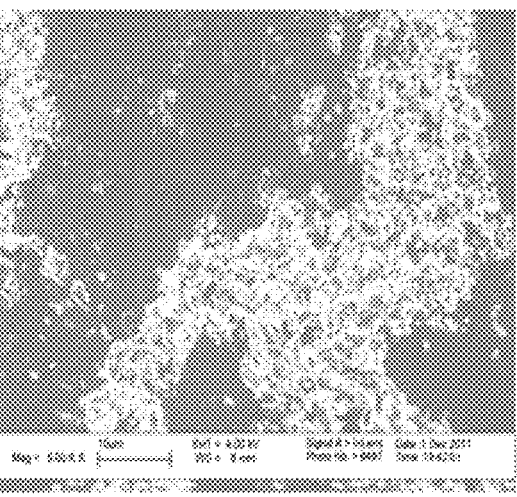
Figure 19E:
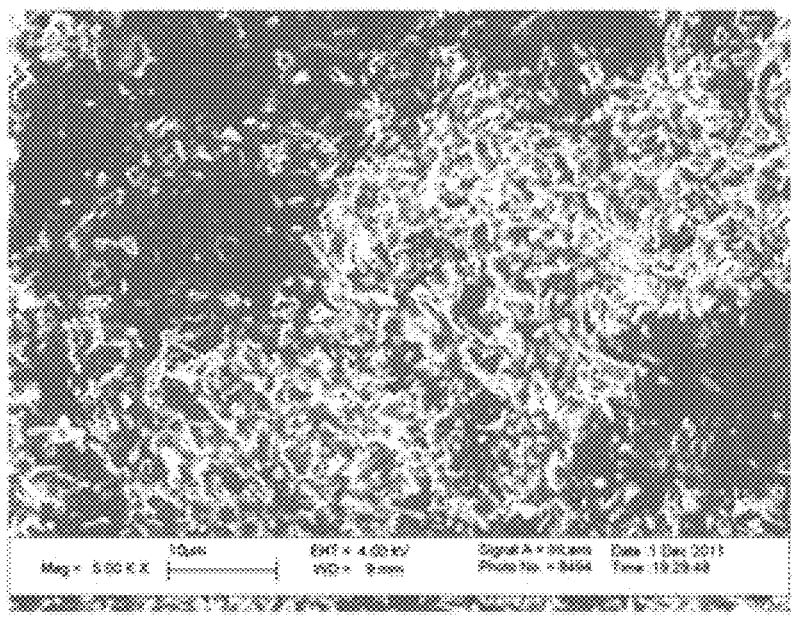
Figure 20A:
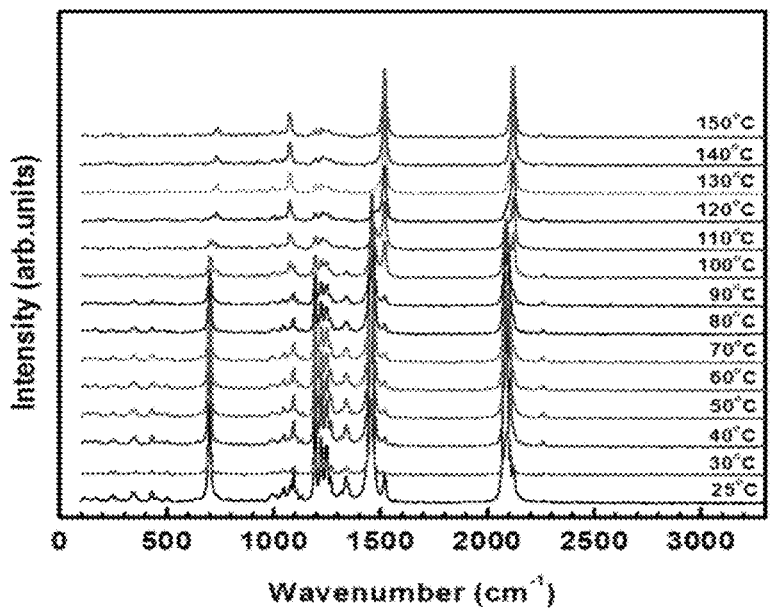
FIGS. 20(a)-(b) are graphical depictions of 785 nm laser excited Raman spectra of pure poly-PCDA as a function of: (a) increasing temperature, and (b) decreasing temperature in accordance with one or more embodiments of the present invention.
Figure 20B:
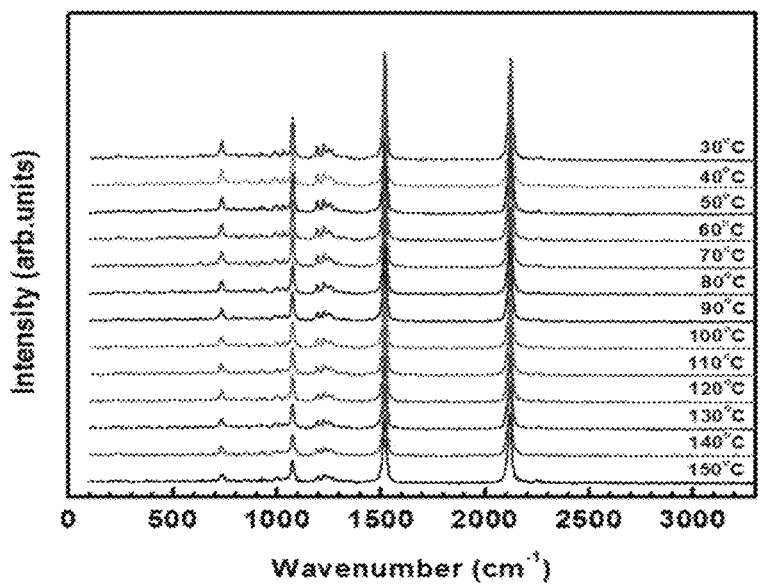
Figure 21A:
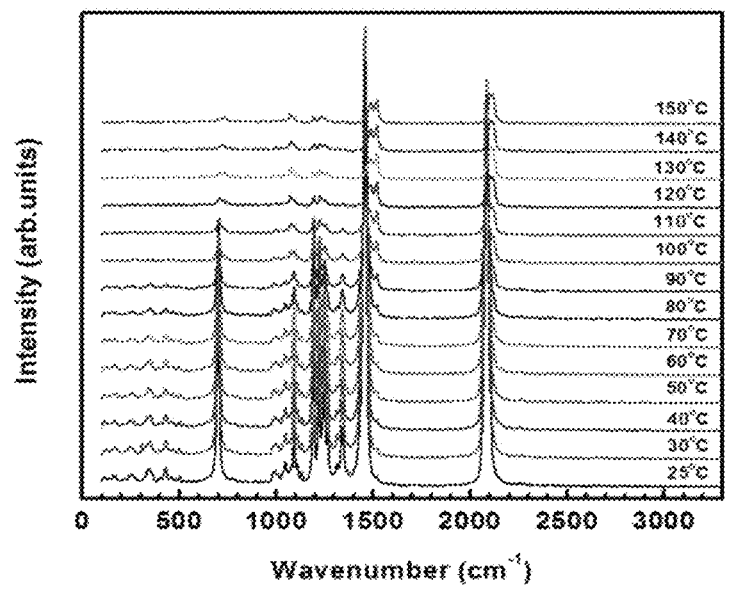
FIGS. 21(a)-(b) are graphical depictions of 785 nm laser excited Raman spectra of pure poly-PCDA/ZnO (5 wt %) as a function of: (a) increasing temperature, and (b) decreasing temperature in accordance with one or more embodiments of the present invention.
Figure 21B:
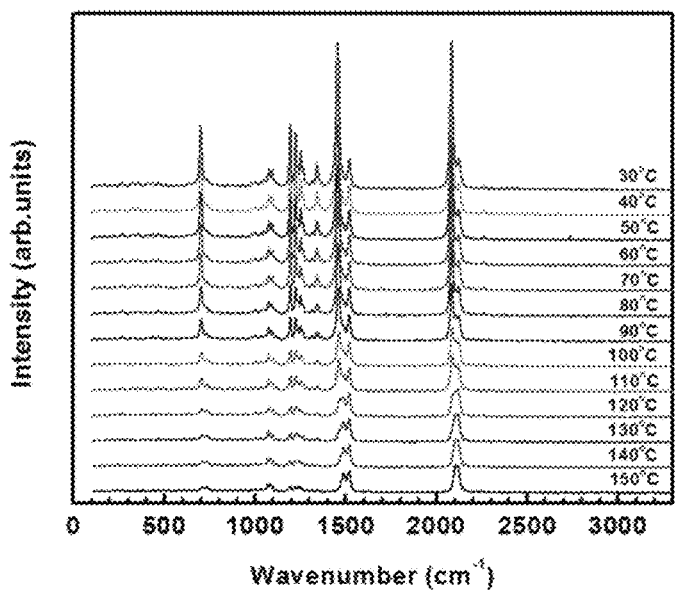
Figure 22A:
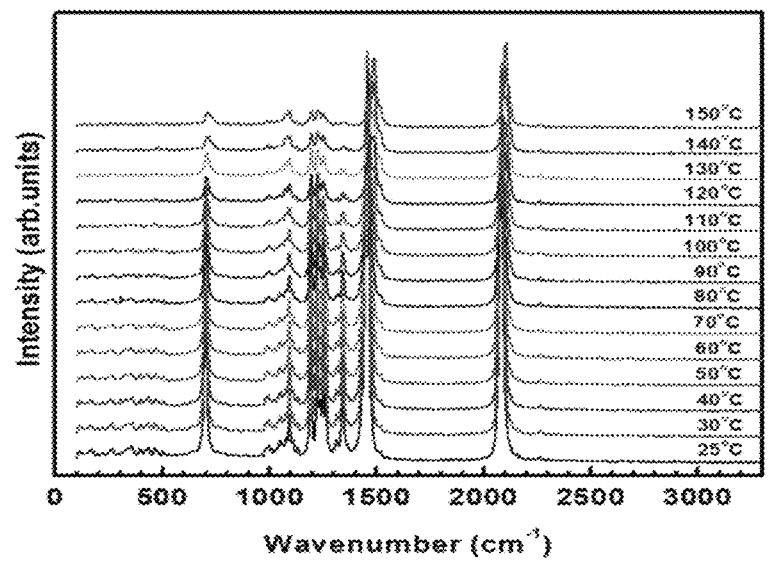
FIGS. 22(a)-(b) are graphical depictions of 785 nm laser excited Raman spectra of pure poly-PCDA/ZnO (10 wt %) as a function of: (a) increasing temperature, and (b) decreasing temperature in accordance with one or more embodiments of the present invention.
Figure 22B:
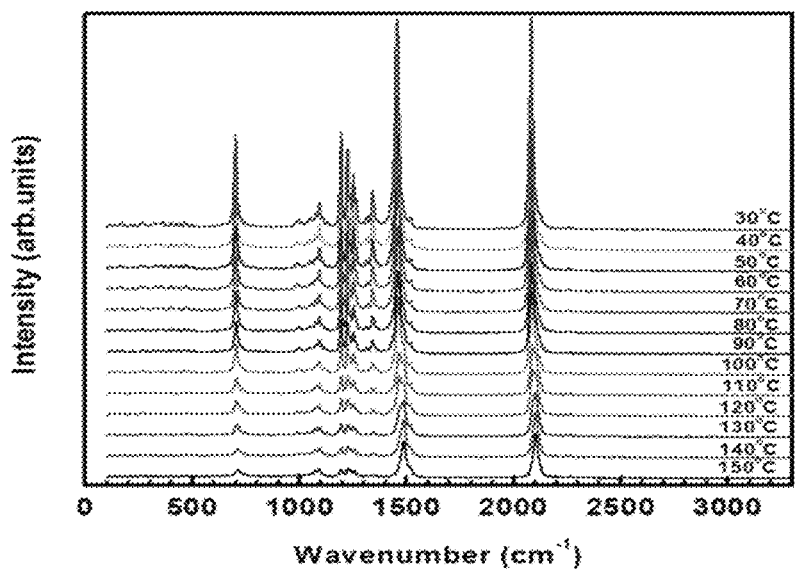
Figure 23A:
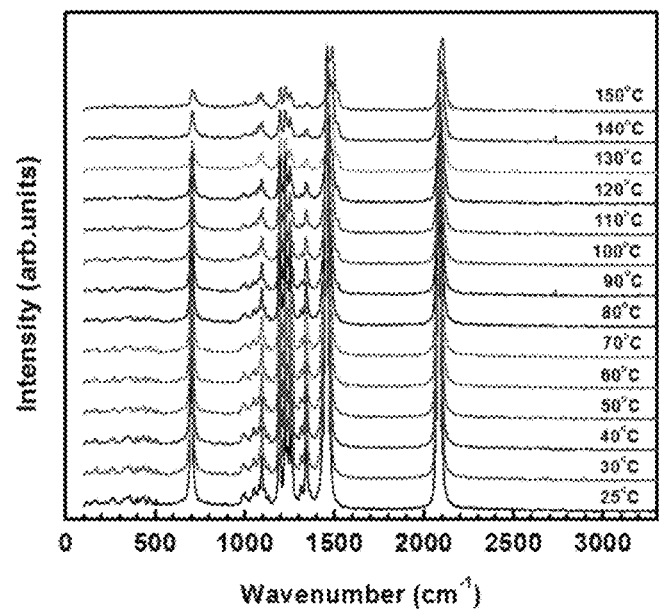
FIGS. 23(a)-(b) are graphical depictions of 785 nm laser excited Raman spectra of pure poly-PCDA/ZnO (15 wt %) as a function of: (a) increasing temperature, and (b) decreasing temperature in accordance with one or more embodiments of the present invention.
Figure 23B:
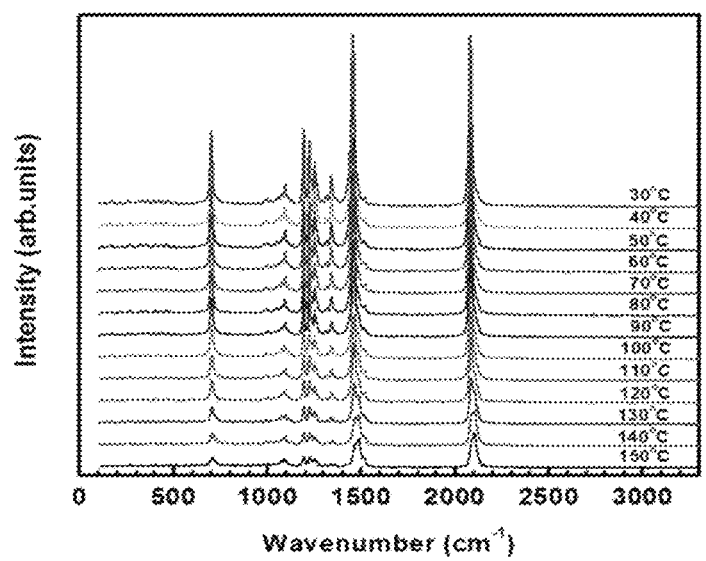

For the sonication power factor, probe sonication and bath sonication methods were selected. By comparison between PCDA undergoing bath sonication and probe sonication (30 min) (See FIGS. 18(a) and (b)), it is clear that probe sonication is more preferable than bath sonication due to the high power input.

The PCDA particle size changes shown by the SEM images with sonication time in FIGS. 19(a)-(e) indicate that the size of the PCDA particles dramatically decreases from the millimeter scale to around 10 µm in the first 15 min.; after that the particle size decreases slowly from ca. 10 µm to ca. 1 µm.

Figure 11A:
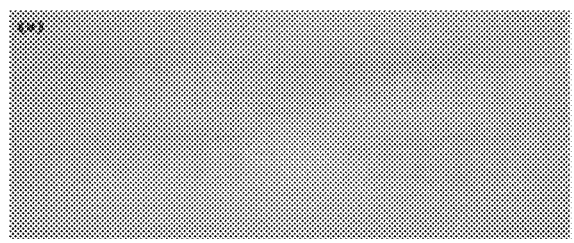
FIGS. 11(a)-(d) are photographic depictions of: (a) inkjet printed PCDA/ZnO composite on a normal paper substrate; (b) inkjet printed PCDA/ZnO composite on a Kapton film substrate; (c) Poly-PCDA/ZnO at 25° C.; and (d) Poly-PCDA/ZnO at 150° C. in accordance with one or more embodiments of the present invention.
Figure 11B:
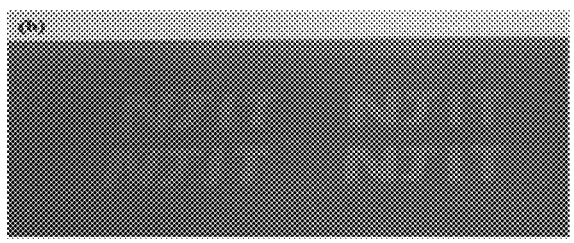
Figure 11C:
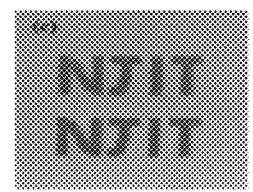
Figure 11D:
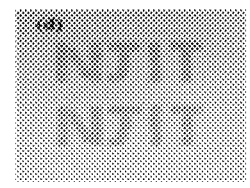

FIG. 11(a) demonstrates that the ink is not visible when it is in the monomer state because PCDA does not absorb visible light. In order to increase the contrast, the ink was jet printed on Kapton film (FIG. 11(b)). However, the polymerization of PCDA initiated by UV-irradiation (254 nm, 1 $mW/cm^2$, 30 s) results in the formation of visually resolvable blue image patterns (FIG. 11(c)). This phenomenon agrees with the observation by Yoon et al. that PDA monomers are well-aligned and closely packed following printing and that the PDAs are indeed formed on the paper substrate. Also, FIGS. 11(c) and (d) show that the reversible color change of poly-PCDA/ZnO can be visually detected.

Thermochromism in Poly-PCDA/ZnO Composites Fabricated by Inkjet Printing.

The molecular interaction on nanocomposite formation was studied by ATR-FTIR spectroscopy at room temperature in both the red and blue phases for poly-PCDA and in the blue phase for poly-PCDA/ZnO composites fabricated by inkjet printing. The inkjet printed PCDA and PCDA/ZnO composites were also investigated by Raman spectroscopy. Details about the molecular structural changes around the chromatic transition temperature were acquired by temperature-dependent Raman spectroscopy of poly-PCDA and poly-PCDA/ZnO composites. The colorimetric changes as a function of temperature are investigated further both by optical densitometry and RGB measurements.

Raman and ATI-FTIR Spectroscopy of Monomer, Polymer and Composites of PCDA.

Figure 12A:
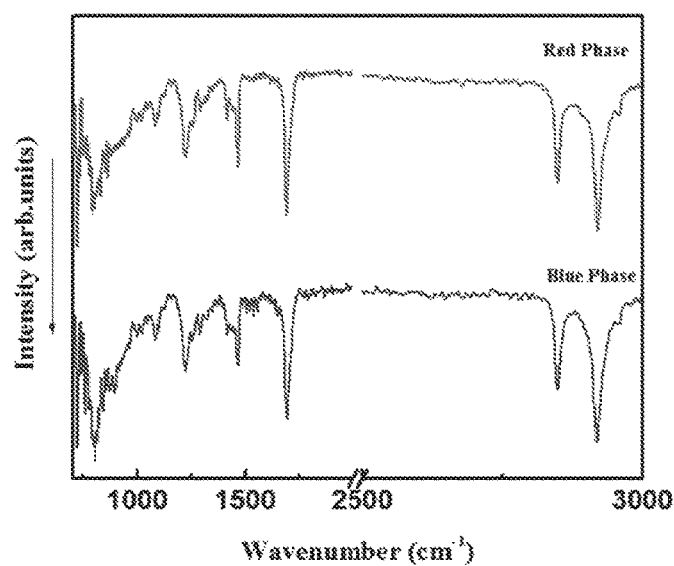
FIGS. 12(a)-(c) are graphical depictions of ATR-FTIR spectra at room temperature of: (a) inkjet printed poly-PCDA in the blue and red phases; (b) and (c) inkjet printed poly-PCDA and poly-PCDA/ZnO composites in the blue phase between 700 and 3000 cm$^{-1}$ and expanded in the 700 and 1900 cm$^{-1}$ spectral range, respectively in accordance with one or more embodiments of the present invention.
Figure 12B:
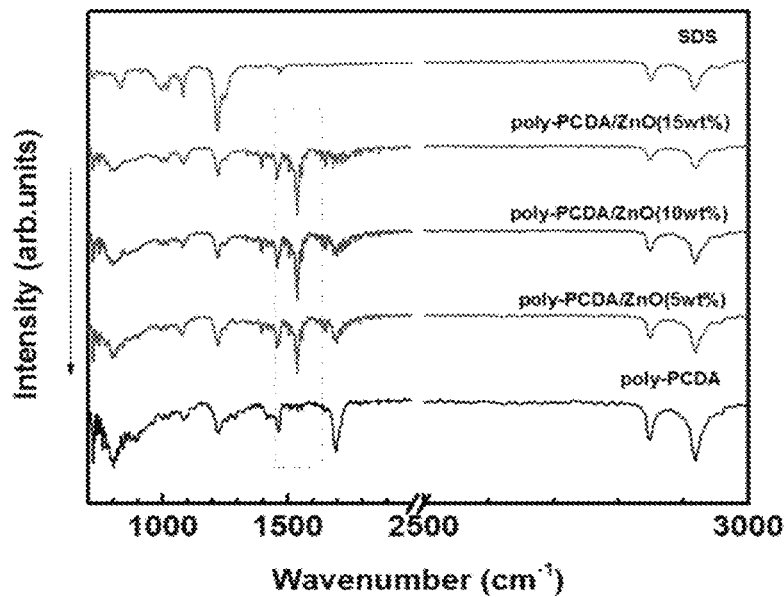
Figure 12C:
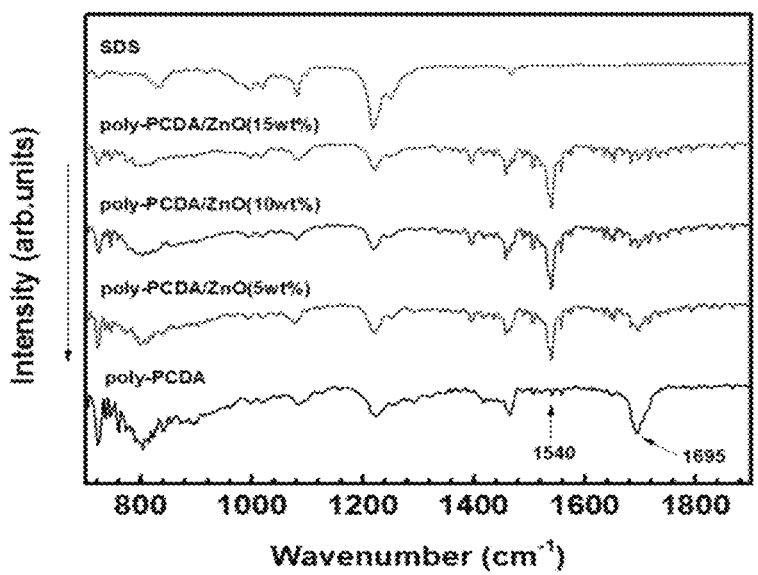

FIG. 12(a) shows the ATR-FTIR spectra of inkjet printed poly-PCDA in its blue and red phases, and FIGS. 12(b) and 12(c) show the spectra of poly-PCDA and poly-PCDA/ZnO composites in the 700 to 3000 $cm^{-1}$ and expanded in the 700 to 1900 $cm^{-1}$ regions, respectively. For poly-PCDA and poly-PCDA/ZnO themselves, the asymmetric and symmetric stretching vibrations lines of the polydiacetylene side chains $CH_2$ groups at ca. 2900 $cm^{-1}$, and the lines at 1465, 1420 and 1695 $cm^{-1}$ are the same as those reported in a previous study. Note that neither the interaction between SDS and poly-PCDA nor that between SDS and poly-PCDA/ZnO composites is observed from AFR-FTIR spectra. Compared with ATR-FTIR spectra of poly-PCDA in FIGS. 14(b) and 14(c), it is obvious that a relatively strong new line shows up in the spectra of poly-PCDA/ZnO composites at 1540 $cm^{-1}$, meanwhile the C=O stretching line at 1695 $cm^{-1}$ decreases in intensity with the increase the concentration of ZnO. The appearance of a line at 1540 $cm^{-1}$ suggests the formation of a chelate between the neighboring side chain —COOH head groups of poly-PCDA and zinc ions from ZnO.

Figure 13A:
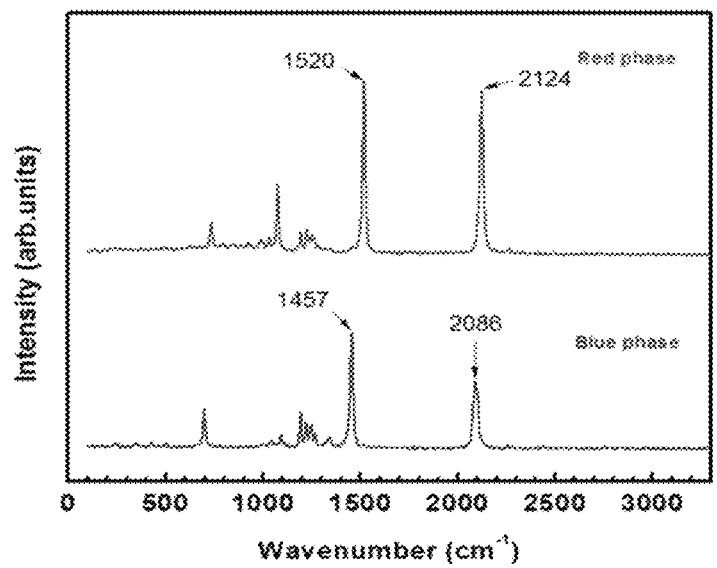
FIGS. 13(a)-(d) are graphical depictions of 785 nm laser-excited Raman spectra of: (a) blue (bottom) and red (top) phases of poly-PCDA at room temperature; (b) blue phase of poly-PCDA and poly-PCDA/ZnO composites with three different ZnO concentrations at ambient temperature; (c) and (d) PCDA and PCDA/ZnO with three different ZnO concentrations and expanded in the 2000 and 2300 cm$^{-1}$ spectral range, respectively in accordance with one or more embodiments of the present invention.

780 nm laser excited Raman spectra were obtained to investigate the resonance-enhanced molecular vibrational modes of the conjugated poly-PCDA backbone. From the Raman spectra in FIG. 13(a) for inkjet printed poly-PCDA, two intense lines at 2086 cm$^{-1}$ and 1457 cm$^{-1}$ in the blue phase, and for the lines at 2124 cm$^{-1}$ and 1520 cm$^{-1}$ in the red phase are assigned to C≡C and C═C stretching vibrations, respectively. It appears that SDS does not affect the phase transition of poly-PCDA. By comparison, the upshift in frequency is due to the irreversible stress on the polymer backbone which could result from the dissociation of the head group hydrogen bonds in the red phase. The Raman lines at frequencies below that of the C═C stretching mode can be assigned to Raman-active deformation and C—C stretching motions of the conjugated polymer backbone mixed with hydrocarbon chain deformation modes. The triplet of lines around 1250 cm$^{-1}$ and the line at 700 cm$^{-1}$ in the blue phase are relatively intense, which is due to resonance enhancement caused by the mixing of the backbone C—C stretching and deformation modes.

Figure 13B:
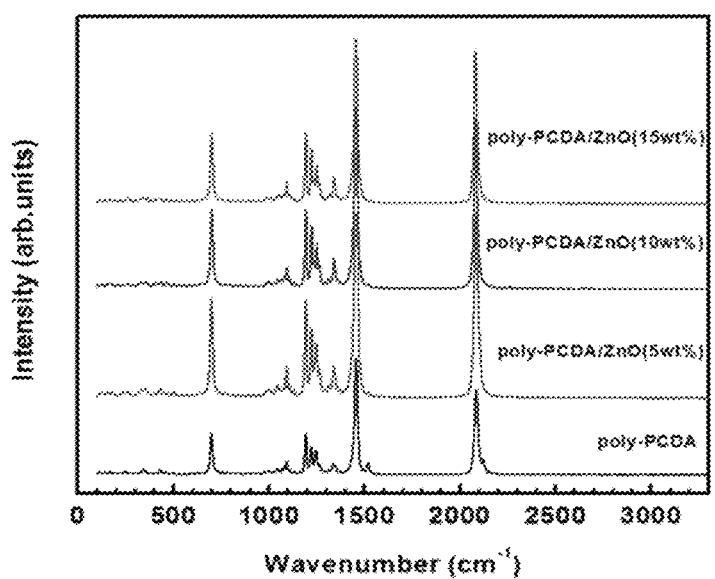

FIG. 13(b) shows the Raman spectrum of the inkjet printed poly-PCDA in the blue phase compared with the blue phase spectra of poly-PCDA/ZnO composites fabricated by inkjet printing. The line at 2262 cm$^{-1}$ appears neither in the spectrum of poly-PCDA nor that of poly-PCDA/ZnO composites in the C≡C stretching mode region of poly-PCDA, which indicates the absence of unconverted PCDA or formation of diyne exists in the PDA/ZnO composites. By contrast, a relatively weak line in the C═C region at 1520 cm$^{-1}$ in the blue phase due to a red phase impurity disappears on composite formation. In comparison with poly-PCDA, another interesting feature which is consistent with the chemical interaction of poly-PCDA with ZnO is that the line at 690 cm$^{-1}$ and the triplet of lines at 1250 cm$^{-1}$ assigned above to largely polymer backbone modes increases substantially in the composite phases. Together with ATR-FTIR results, it is clear that the SDS would not affect the functional group of poly-PCDA, and the chelation between ZnO and poly-PCDA.

Figure 13C:
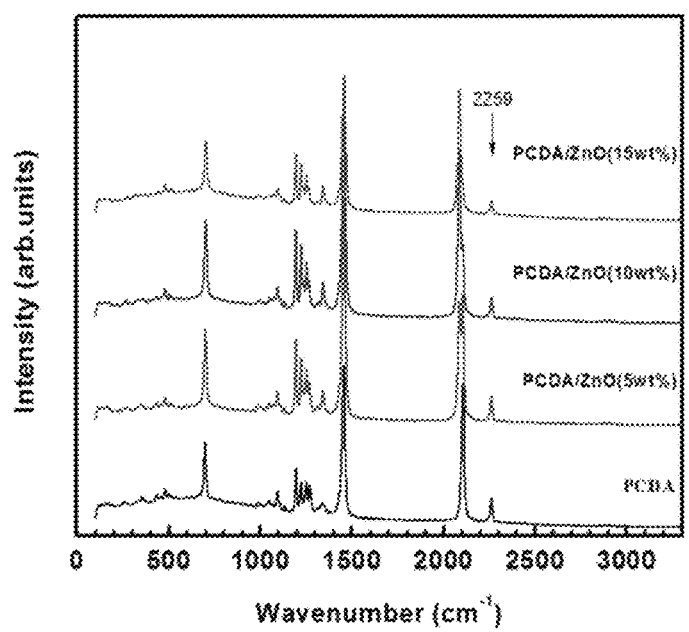
Figure 13D:
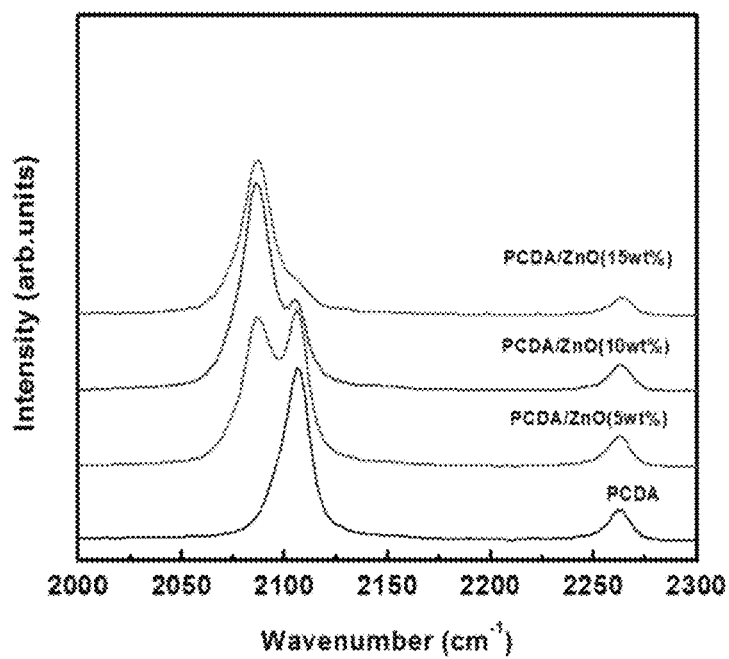

Since no vibration intensity variation of COO$^-$ and COOH for different ZnO concentrations was reported in the work done of Patlolla et al., Thermochromism in Polydiacetylene-Metal Oxide Nanocomposites, J Mater Chem, 22(2012) 7028-35, and the concentration of ZnO could affect the chromatic property of poly-PCDA, further investigation was carried out to study the effect of ZnO concentration on the PCDA system. The Raman spectra obtained for inkjet printed PCDA and PCDA/ZnO composites are shown in FIG. 13(c). The line at 2259 cm$^{-1}$ appearing in PCDA and PCDA/ZnO composites could be assigned to the acetylene of PCDA, and the lines at 1457 cm$^{-1}$ and 2107 cm$^{-1}$ in PCDA could be due to the C═C and C≡C stretching modes, respectively, from polymerized PCDA. The frequency discrepancies between polymerized PCDA in PCDA and poly-PCDA could be due to the low polymerization degree of PCDA which gives weaker conjugation effect. With the adding of ZnO, a new line shows up at 2086 cm$^{-1}$. From FIG. 13(d) it can be observed that in the PCDA sample with 5 wt % ZnO the line at 2086 cm$^{-1}$ almost bears the same intensity of the one at 2107 cm$^{-1}$, then it increases in intensity with the increase of ZnO concentration. By comparing with the Raman spectra of poly-PCDA and poly-PCDA/ZnO composites, the line at 2086 cm$^{-1}$ could be caused by the C≡C stretching modes of poly-PCDA blue phase, and the one at 2107 cm$^{-1}$ could be assigned to the stretching modes C≡C of poly-PCDA red phase. Based on the ATR-FTIR results, chelates formed between ZnO and PCDA. The interaction of carbonyl head group of PCDA with Zn ion of ZnO in acid environment could enhance the formation of the blue phase poly-PCDA, meanwhile inhibiting the formation of the red phase of poly-PCDA.

Temperature-Dependent Raman Spectroscopy of Poly-PCDA and Poly-PCDA/ZnO Composites Fabrication by Inkjet Printing Method.

Figure 15A:
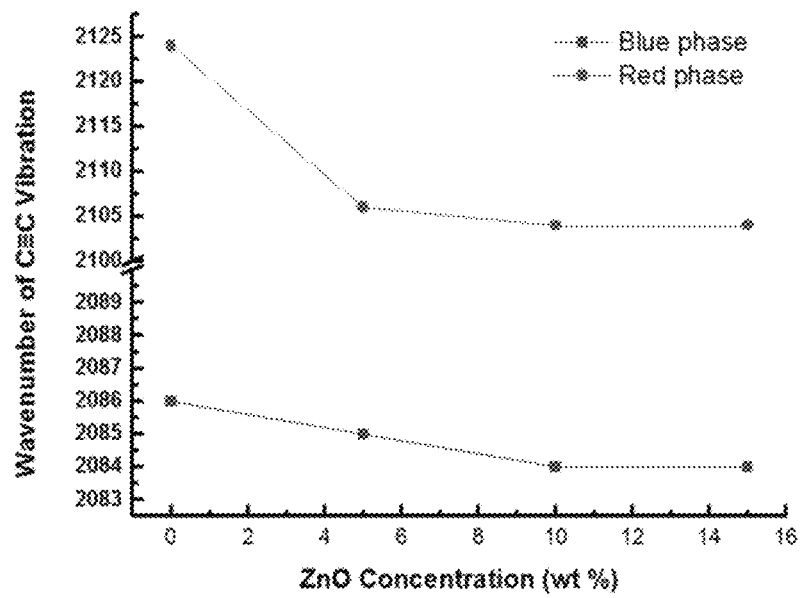
FIGS. 15(a)-(b) are graphical depictions of (a) C≡C stretching mode; and (b) C=C and substantially C—C stretching mode frequencies as a function of ZnO concentration (in the blue phase and the red phase of poly-PCDA/ZnO) in accordance with one or more embodiments of the present invention.
Figure 15B:
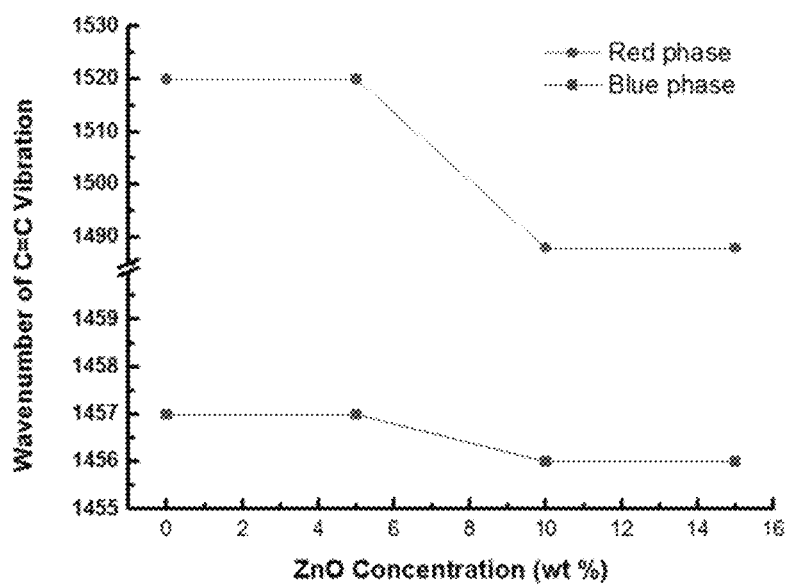

The effect of ZnO on the poly-PCDA was further investigated by temperature-dependent Raman spectra for poly-PCDA and poly-PCDA/ZnO composites, the spectra of which are shown in FIGS. 20(a)-23(b). The test temperature range was from 25° C. to 150° C. in increments of 10° C. After reaching 150° C., data was collected for the cool down process at the same temperature values as the heating process. With reference to FIGS. 14(a)-(d), since C≡C and C═C vibrations are the two major characteristic peaks to study the chromatic properties of PDA, the frequencies of stretching vibration for C≡C and C═C of poly-PCDA and poly-PCDA/ZnO composites as a function of temperature cycling were plotted. The frequency upshift in the red phase decreases with increasing ZnO concentration, suggesting that the stress on the polymer backbone is lowered due to chelation of ZnO with the head group of poly-PCDA to make the chromatic transition reversible. FIGS. 14(a)-(d) indicate increases in frequencies at the chromatic blue to red transition at 100° C. on heating for pure poly-PCDA and around 120° C., 130° C. and 140° C., respectively, for poly-PCDA/ZnO composites with different ZnO concentrations. Upon cooling, decreases in frequencies occur at 110° C., 120° C., 130° C. for each corresponding poly-PCDA/ZnO composite material, which corresponds to the intensity increase of COO$^-$ suggested by ATR-FTIR spectra. Together with C≡C and C═C wavenumber as a function of ZnO concentration in both blue and red phase (FIGS. 15(a)-(b)), it can be inferred that with the increase of ZnO concentration, the amount of chelation would be saturated once it reaches a certain point.

Colorimetric Measurements.

Colorimetric performance of poly-PCDA and poly-PCDA/ZnO composites were investigated from two aspects: (a) Optical densitometry measurements of the chromaticity as function of temperature, (b) Red, Green and Blue (RGB) measurements of different inkjet printed indicators (5 layers inkjet printed on 5 mm×5 mm square substrates).

Optical Densitometry.

Figure 16A:
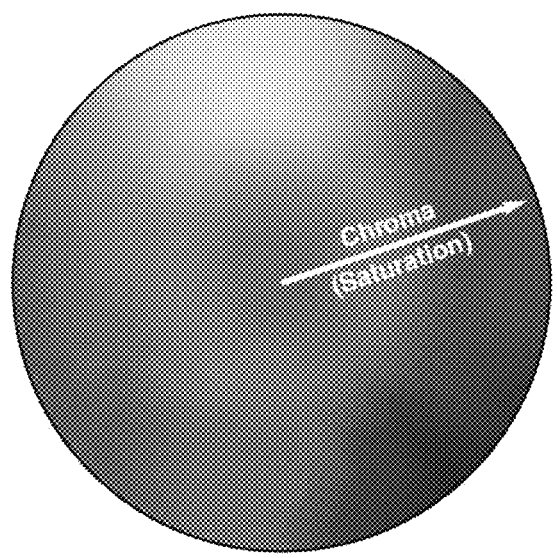
FIGS. 16(a)-(c) are graphical depictions of (a) chromaticity (chroma) distribution from gray (dull) color at the center to saturated (vivid) color at the perimeter (arrows indicate chromatic transition temperatures discussed in the text); (b) chromaticity versus temperature plots for poly-PCDA and poly-PCDA/ZnO composites of three different compositions; (c) chromaticity of poly-PCDA/ZnO composites as a function of thermal cycle in accordance with one or more embodiments of the present invention.
Figure 16B:
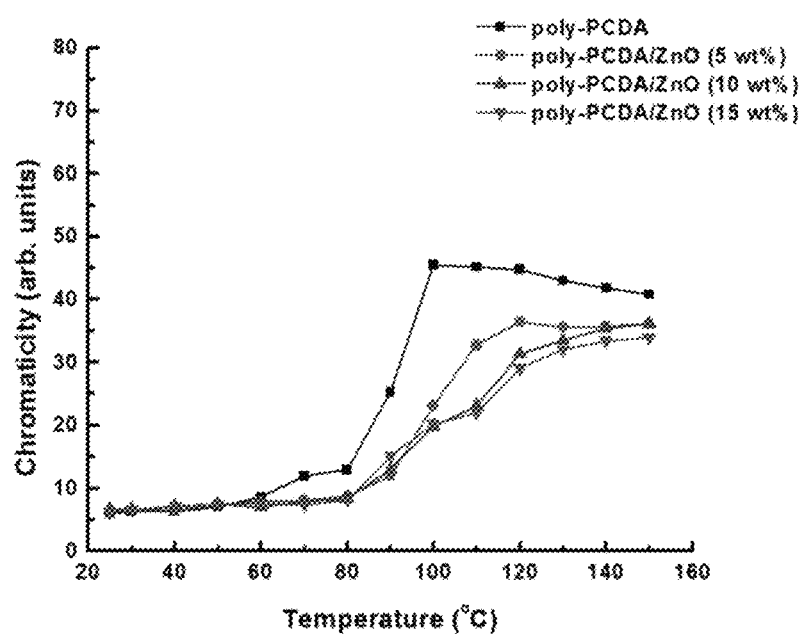
Figure 16C:
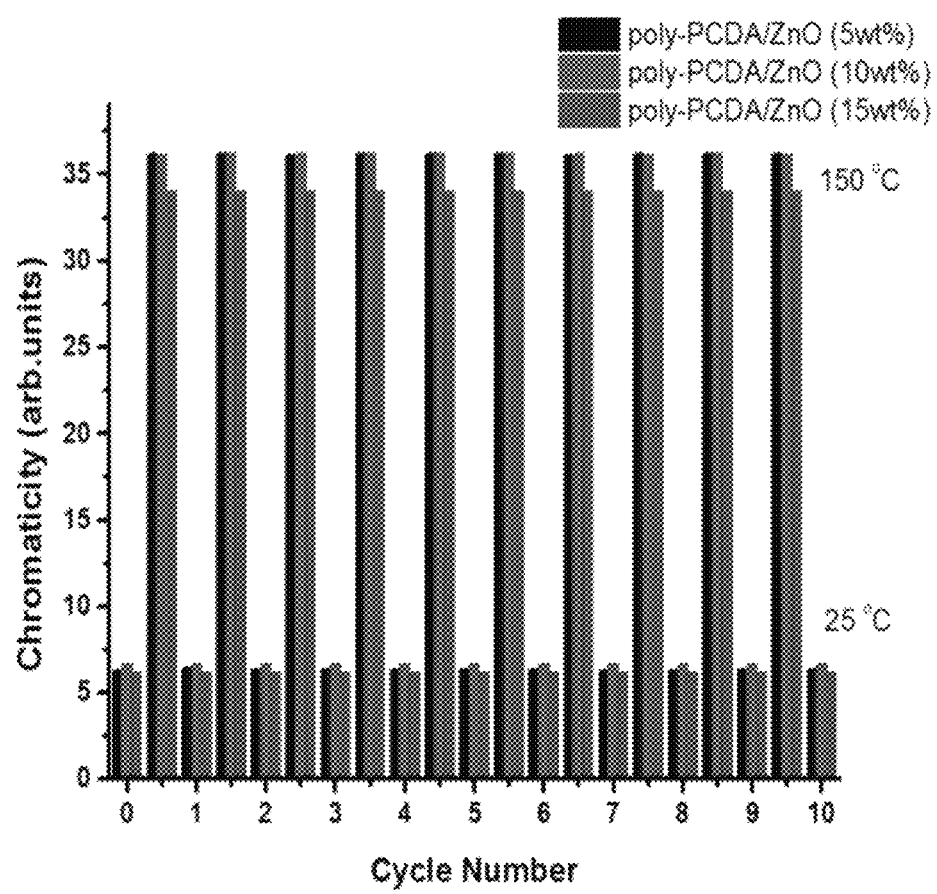

The chromaticity or chroma describes the dullness or vividness of a color, in other words, how close the color is to either gray or the pure hue (FIG. 16(a)). The changes in chromaticity as a function of temperature for poly-PCDA and poly-PCDA/ZnO composites are shown in FIG. 16(b). The rapid increase followed by a drop of the chromaticity of the pure polymer is caused by the chromatic transition near 100° C. The addition of 5 wt % ZnO increases the chromatic transition to 120° C. consistent with the Raman data. The poly-PCDA/ZnO composites with 10 wt % and 15 wt % ZnO show almost the same changes in chromaticity as a function of temperature. This indicates that chelate formation between the PCDA side chain head groups and ZnO had reached a saturation level for these composites. FIG. 16(c) shows excellent reversibility in chromaticity as a function of the number of cycles from 25° C. to 150° C. indicating that the nanocomposite can function as a very reproducible thermal sensor.

RGB Measurements.

Figure 17A:
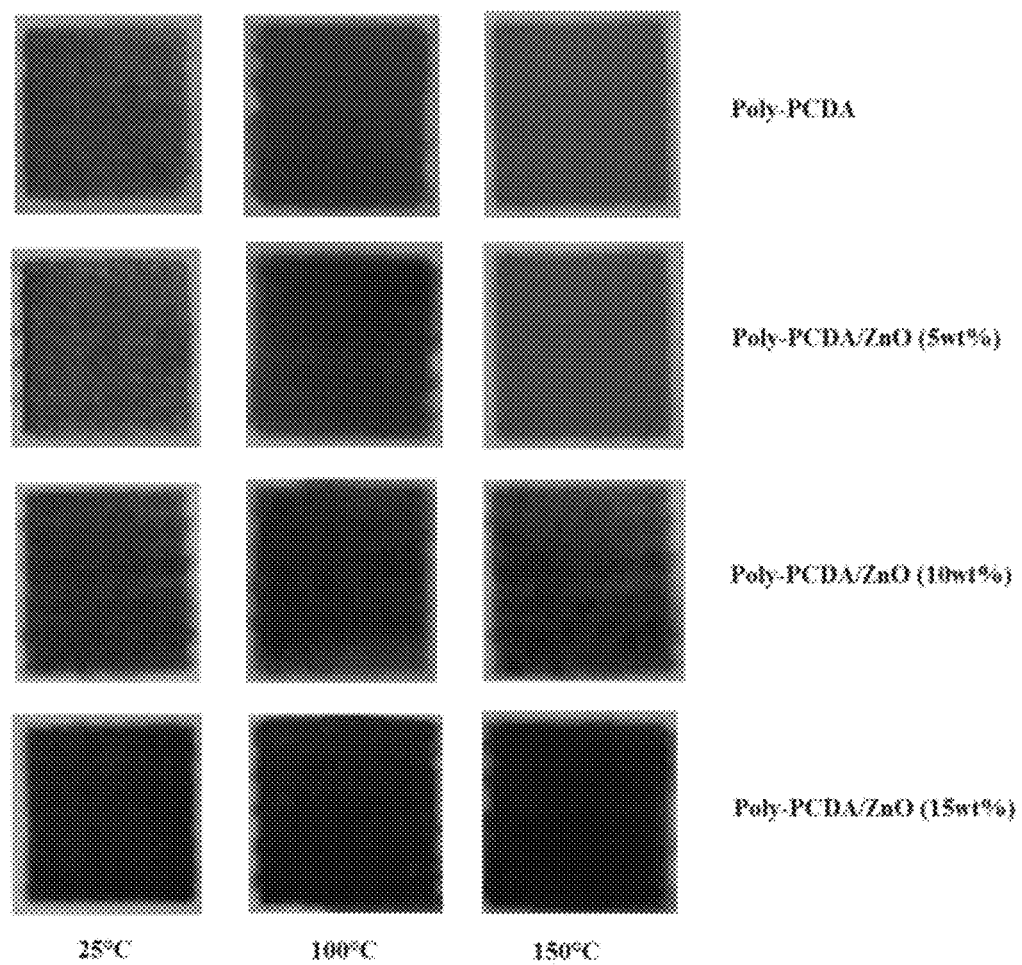
FIGS. 17(a)-(b) are (a) an array of cropped photographic images of PCDA and PCDA/ZnO composites fabricated by inkjet printing on normal paper at different temperatures; and (b) a histogram of RGB values of the photographic images analyzed by software in accordance with one or more embodiments of the present invention.

Now referring to FIG. 17(a), photographic images of PCDA or PCDA/ZnO as a function of temperature clearly show the color changes with increase of ZnO concentration.

Figure 17B:
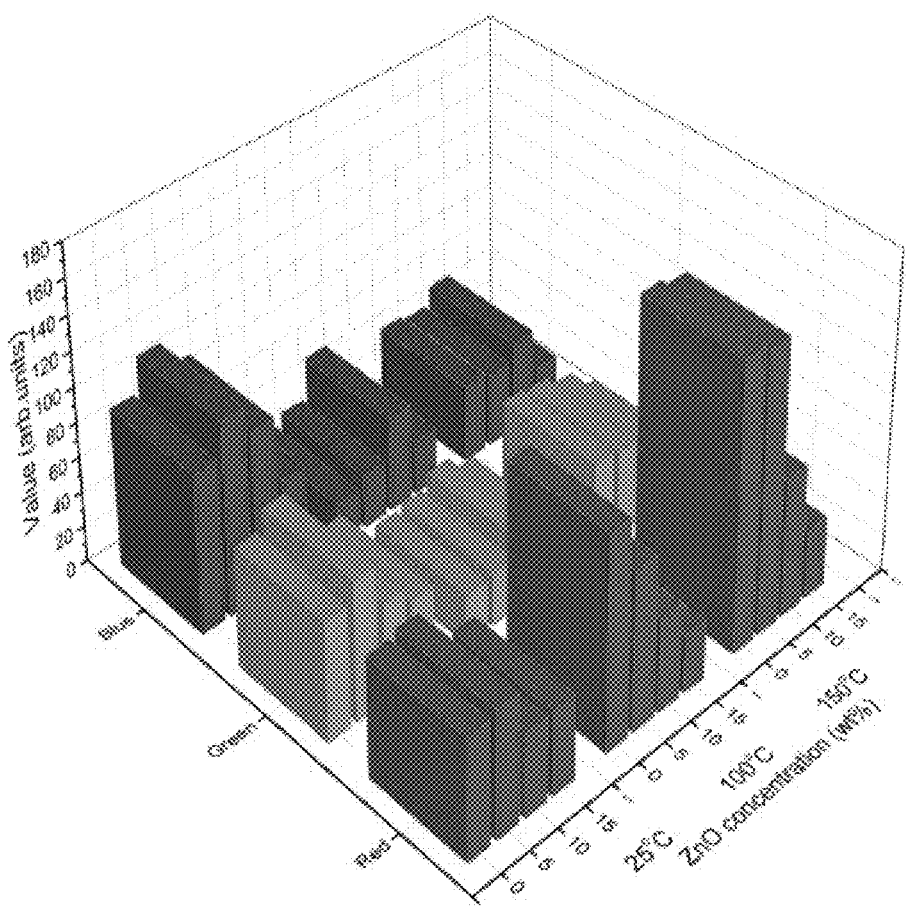

The colored images on normal paper were quantitatively analyzed by a photographic processing software to obtain the RGB values with the histogram of RGB values showing a distinguishable color change with increase of ZnO concentration (FIG. 17(b)) due to the improved color contrast in the blue phase of poly-PCDA. With the increase of ZnO concentration from 0~10 wt % the red value decreases whereas the blue value increases, with this effect becoming more obvious at higher temperatures.

The ATR-FTIR results indicate that the SDS surfactant does not react with either poly-PCDA or poly-PCDA/ZnO, and SDS does not interfere with the chelate formation. Temperature-dependent Raman spectra indicate that the temperature where the Raman-active $\upsilon(C\equiv C)$ and $\upsilon(C=C)$ vibration peak frequencies show an upshift, increases with increasing ZnO content. From the Raman spectra of PCDA/ZnO samples, it can be seen that ZnO enhances the formation of blue poly-PCDA by inhibiting the formation of red poly-PCDA. Colorimetric measurements demonstrate a distinguishable colorimetric change with increase of ZnO concentration, and excellent color change reversibility for poly-PCDA/ZnO composites. Also, the success of inkjet printing poly-PCDA/ZnO composites film provides a fast and economic method to broaden the application of PDAs on various substrates.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention. All references cited and/or listed herein are incorporated by reference herein in their entireties.

REFERENCES

[1] A. B. Descalzo, M. Dolores Marcos, C. Monte, R. Martinez-Manez, K. Rurack, Mesoporous Silica Materials With Covalently Anchored Phenoxazinone Dyes as Fluorescent Hybrid Materials for Vapour Sensing, J Mater Chem, 17(2007) 4716-23.

[2] M. C. Janzen, J. B. Ponder, D. P. Bailey, C. K. Ingison, K. S. Suslick, Colorimetric Sensor Arrays for Volatile Organic Compounds, Anal Chem, 78(2006) 3591-600.

[3] Y. Lu, Y. Yang, A. Sellinger, M. Lu, J. Huang, H. Fan, et al., Self-Assembly of Mesoscopically Ordered Chromatic Polydiacetylene/Silica Nanocomposites, Nature, 410 (2001) 913-7.

[4] M. L. Muro, C. A. Daws, F. N. Castellano, Microarray Pattern Recognition Based on PtII Terpyridyl Chloride Complexes: Vapochromic and Vapoluminescent Response, Chem Commun, (2008) 6134-6.

[5] N. A. Rakow, K. S. Suslick, A Colorimetric Sensor Array for Odour Visualization, Nature, 406(2000) 710-3.

[6] T. Champaiboon, G. Tumcharern, A. Potisatityuenyong, S. Wacharasindhu, M. Sukwattanasinitt, A polydiacetylene multilayer film for naked eye detection of aromatic compounds, Sensors and Actuators B: Chemical, 139 (2009) 532-7.

[7] H. Jiang, Y. Wang, Q. Ye, G. Zou, W. Su, Q. Zhang, Polydiacetylene-based colorimetric sensor microarray for volatile organic compounds, Sensors and Actuators B: Chemical, 143(2010) 789-94.

[8] S. Pumtang, W. Siripornnoppakhun, M. Sukwattanasinitt, A. Ajavakom, Solvent colorimetric paper-based polydiacetylene sensors from diacetylene lipids, J Colloid Interface Sci, 364(2011) 366-72.

[9] P. T. Hammond, M. F. Rubner, Thermochromism in Liquid Crystalline Polydiacetylenes, Macromolecules, 30(1997) 5773-82.

[10] X. Huang, S. Jiang, M. Liu, Metal Ion Modulated Organization and Function of the Langmuir-Blodgett Films of Amphiphilic Diacetylene: Photopolymerization, Thermochromism, and Supramolecular Chirality, J Phys Chem B, 109(2004) 114-9.

[11] H. Peng, J. Tang, J. Pang, D. Chen, L. Yang, H. S. Ashbaugh, et al., Polydiacetylene/Silica Nanocomposites with Tunable Mesostructure and Thermochromatism from Diacetylenic Assembling Molecules, J Am Chem Soc, 127(2005) 12782-3.

[12] J. M. Kim, Y. B. Lee, S. K. Chae, D. J. Ahn, Patterned Color and Fluorescent Images with Polydiacetylene Supramolecules Embedded in Poly(vinyl alcohol) Films, Adv Funct Mater, 16(2006) 2103-9.

[13] S. Lee, J. M. Kim, Alpha-Cyclodextrin: A Molecule for Testing Colorimetric Reversibility of Polydiacetylene Supramolecules, Macromolecules, 40(2007) 9201-4.

[14] H. Park, J. S. Lee, H. Choi, D. J. Ahn, J. M. Kim, Rational Design of Supramolecular Conjugated Polymers Displaying Unusual Colorimetric Stability upon Thermal Stress, Adv Funct Mater, 17(2007) 3447-55.

[15] D. N. Batchelder, S. D. Evans, T. L. Freeman, L. Haeussling, H. Ringsdorf, H. Wolf, Self-Assembled Monolayers containing Polydiacetylenes, J Am Chem Soc, 116(1994) 1050-3.

[16] R. H. Baughman, Solid-state polymerization of diacetylenes, J Appl Phys, 43(1972) 4362-70.

[17] W. C. Robert, Y. S. Darryl, S. M. Matthew, M. A. Eriksson, R. B. Alan, Polydiacetylene Films: A Review of Recent Investigations into Chromogenic Transitions and Nanomechanical Properties, J Phys: Condens Matter, 16(2004) R679-R97.

[18] A. Chanakul, N. Traiphol, R. Traiphol, Controlling the reversible thermochromism of polydiacetylene/zinc oxide nanocomposites by varying alkyl chain length, J Colloid Interface Sci, 389(2013) 106-14.

[19] N. Charoenthai, T. Pattanatornchai, S. Wacharasindhu, M. Sukwattanasinitt, R. Traiphol, Roles of head group architecture and side chain length on colorimetric response of polydiacetylene vesicles to temperature, ethanol and pH, J Colloid Interface Sci, 360(2011) 565-73.

[20] M. Gou, G. Guo, J. Zhang, K. Men, J. Song, F. Luo, et al., Time—temperature chromatic sensor based on polydiacetylene (PDA) vesicle and amphiphilic copolymer, Sensors and Actuators B: Chemical, 150(2010) 406-11.

[21] S. Ryu, I. Yoo, S. Song, B. Yoon, J.-M. Kim, A Thermoresponsive Fluorogenic Conjugated Polymer for a Temperature Sensor in Microfluidic Devices, J Am Chem Soc, 131(2009) 3800-1.

[22] N. Traiphol, N. Rungruangviriya, R. Potai, R. Traiphol, Stable polydiacetylene/ZnO nanocomposites with two-steps reversible and irreversible thermochromism: The influence of strong surface anchoring, J Colloid Interface Sci, 356(2011) 481-9.

[23] H. Peng, X. Sun, F. Cai, X. Chen, Y. Zhu, G. Liao, et al., Electrochromatic carbon nanotube/polydiacetylene nanocomposite fibres, Nat Nano, 4(2009) 738-41.

[24] B. Yoon, D.-Y. Ham, O. Yarimaga, H. An, C. W. Lee, J.-M. Kim, Inkjet Printing of Conjugated Polymer Precursors on Paper Substrates for Colorimetric Sensing and Flexible Electrothermochromic Display, Adv Mater, 23(2011) 5492-7.

[25] E. Gatebe, H. Herron, R. Zakeri, P. Ramiah Rajasekaran, S. Aouadi, P. Kohli, Synthesis and Characterization of Polydiacetylene Films and Nanotubes, Langmuir, 24(2008) 11947-54.

[26] A. Patlolla, J. Zunino, A. I. Frenkel, Z. Iqbal, Thermochromism in Polydiacetylene-Metal Oxide Nanocomposites, J Mater Chem, 22(2012) 7028-35.

[27] A. Wu, C. Beck, Y. Ying, J. Federici, Z. Iqbal, Thermochromism in Polydiacetylene-ZnO Nanocomposites, The Journal of Physical Chemistry C, 117(2013) 19593-600.

[28] B. J. de Gans, P. C. Duineveld, U. S. Schubert, Inkjet Printing of Polymers: State of the Art and Future Developments, Adv Mater, 16(2004) 203-13.

[29] T. H. J. van Osch, J. Perelaer, A. W. M. de Laat, U. S. Schubert, Inkjet Printing of Narrow Conductive Tracks on Untreated Polymeric Substrates, Adv Mater, 20(2008) 343-5.

[30] Y. Oh, J. Kim, Y. J. Yoon, H. Kim, H. G. Yoon, S.-N. Lee, et al., Inkjet printing of Al2O3 dots, lines, and films: From uniform dots to uniform films, Current Applied Physics, 11(2011) S359-S63.

[31] J. K. Lee, U. J. Lee, M.-K. Kim, S. H. Lee, K.-T. Kang, Direct writing of semiconducting polythiophene and fullerene derivatives composite from bulk heterojunction solar cell by inkjet printing, Thin Solid Films, 519(2011) 5649-53.

[32] U. Zschieschang, T. Yamamoto, K. Takimiya, H. Kuwabara, M. Ikeda, T. Sekitani, et al., Organic Electronics on Banknotes, Adv Mater, 23(2011) 654-8.

[33] A. Russo, B. Y. Ahn, J. J. Adams, E. B. Duoss, J. T. Bernhard, J. A. Lewis, Pen-on-Paper Flexible Electronics, Adv Mater, 23(2011) 3426-30.

[34] M. C. Barr, J. A. Rowehl, R. R. Lunt, J. Xu, A. Wang, C. M. Boyce, et al., Direct Monolithic Integration of Organic Photovoltaic Circuits on Unmodified Paper, Adv Mater, 23(2011) 3500-5.

[35] J. Jang, J. Ha, J. Cho, Fabrication of Water-Dispersible Polyaniline-Poly(4-styrenesulfonate) Nanoparticles For Inkjet-Printed Chemical-Sensor Applications, Adv Mater, 19(2007) 1772-5.

[36] J.-H. Kang, Z. Xu, S.-M. Paek, F. Wang, S.-J. Hwang, J. Yoon, et al., A Dual-Polymer Electrochromic Device with High Coloration Efficiency and Fast Response Time: Poly(3,4-(1,4-butylene-(2-ene)dioxy)thiophene)-Polyaniline ECD, Chemistry—An Asian Journal, 6(2011) 2123-9.

[37] A. C. Siegel, S. T. Phillips, M. D. Dickey, N. Lu, Z. Suo, G. M. Whitesides, Printable Electronics: Foldable Printed Circuit Boards on Paper Substrates (Adv. Funct. Mater. 1, 2010), Adv Funct Mater, 20(2010) n/a-n/a.

[38] M. Wenzel, G. H. Atkinson, Chromatic properties of polydiacetylene films, J Am Chem Soc, 111(1989) 6123-7.

[39] C. Lim, D. J. Sandman, M. Sukwattanasinitt, Topological Polymerization of tert-Butylcalix[4]arenes Containing Diynes, Macromolecules, 41(2007) 675-81.

What is claimed is:

1. A composition comprising a polydiacetylene (PDA) selected from the group consisting of 10,12-pentacosadiynoic acid (PCDA) and 10,12-docosadiynedioic acid (DCDA) and ZnO nanoparticles wherein the ZnO nanoparticles are unalloyed and have an average particle size of 0.01-99 nm wherein the composition comprises greater than 90 wt % of the PDA and less than 10 wt % ZnO nanoparticles.

2. The composition according to claim 1 comprising at least 5 wt % of ZnO nanoparticles.

3. The composition according to claim 1 wherein the ZnO nanoparticles have an average particle size of 0.1-99 nm.

4. The composition according to claim 1 wherein the ZnO nanoparticles have an average particle size of 0.1-15 nm.

5. The composition according to claim 1 consisting of greater than 90 wt % of PDA and less than 10 wt % of ZnO nanoparticles.

6. The composition according to claim 1 wherein the PDA comprises a poly-PDA.

7. A chemical sensor comprising a film comprising a PDA selected from the group consisting of PCDA and DCDA and ZnO nanoparticles disposed on a substrate wherein the ZnO nanoparticles are unalloyed and have an average particle size of 0.01-99 nm wherein the film comprises greater than 90 wt % of the PDA and less than 10 wt % of ZnO nanoparticles.

8. The chemical sensor according to claim 7 wherein the film consists of the PDA and less than 10 wt % of ZnO nanoparticles.

9. A thermochromically reversible composition comprising PCDA and unalloyed ZnO nanoparticles having an average particle size of 0.01-99 nm wherein the thermochromically reversible composition comprises greater than 90 wt % of PCDA and less than 10 wt % ZnO nanoparticles.

10. The thermochromically reversible composition according to claim 9 comprising at least 5% ZnO by weight of the composition.

11. The thermochromically reversible composition according to claim 9 consisting of greater than 90% PCDA and less than 10% ZnO nanoparticles by weight of the composition.

12. A thermochromically reversible film sensor comprising a film comprising the composition of claim 9 formed on a substrate.

* * * * *